US 6,589,769 B1

(12) United States Patent
Xu et al.

(10) Patent No.: US 6,589,769 B1
(45) Date of Patent: Jul. 8, 2003

(54) **METHOD FOR CLONING AND EXPRESSION OF TSPRI RESTRICTION ENDONUCLEASE AND TSPRI METHYLASE IN *E. COLI***

(75) Inventors: Shuang-yong Xu, Lexington, MA (US); Andrew Dore, Salem, MA (US); Michael Dalton, Manchester, MA (US); Jack Benner, South Hamilton, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 10/037,927

(22) Filed: Oct. 19, 2001

(51) Int. Cl.⁷ .............................. C12N 9/22; C12N 15/55
(52) U.S. Cl. ................ 435/199; 435/320.1; 435/252.3; 536/23.2
(58) Field of Search .............................. 435/199, 320.1, 435/252.3; 536/23.2

(56) References Cited

U.S. PATENT DOCUMENTS 5,200,333 A    4/1993  Wilson ..................... 435/172.7
5,498,535 A    3/1996  Fomenkov et al. ....... 435/172.3

OTHER PUBLICATIONS

Blumenthal, et al., J. Bacteriol. 164:501–509 (1985).
Bougueleret, et al., Nuc. Acids Res. 12:3659–3676 (1984).
Fomenkov, et al., Nucl. Acids Res. 22:2399–2403 (1994).
Gingeras and Brooks, Proc. Natl. Acad. Sci. USA 80:402–406 (1983).
Janulaitis, et al., Gene 20:197–204 (1982).
Kiss and Baldauf, Gene 21:111–1119 (1983).
Kiss, et al., Nucl. Acids Res. 13:6403–6421 (1985).
Kosykh, et al., Mol. Gen. Genet. 178:717–719 (1980).
Malone, et al., J. Mol. Biol. 253:618–632 (1995).
Mann, et al., Gene 3:97–112 (1978).
Matsudaira, et al. J. Biol. Chem. 262:10035–10038 (1987).
Roberts and Macelis, Nucl. Acids Res. 27:312–313 (1999).
Schumann, et al., J. Mol. Biol. 257:949–959 (1996).
Szomolanyi, et al., Gene 10:219–225 (1980).
Theriault and Roy, Gene 19:355–359 (1982).
Waite–Rees, et al., J. Bacteriology, 173:5207–5219 (1991).
Walder, et al., J. Biol. Chem. 258:1235–1341 (1983).
Walder, et al., Proc. Nat. Acad. Sci. 78:1503–1507 (1981).
Wayne, et al., Gene 202:83–89 (1997).

*Primary Examiner*—Charles L. Patterson, Jr.
(74) *Attorney, Agent, or Firm*—Gregory D. Williams

(57) ABSTRACT

The present invention relates to recombinant DNA that encodes the TspRI restriction endonuclease as well as TspRI methylase, expression of TspRI restriction endonuclease and TspRI methylase in *E. coli* cells containing the recombinant DNA.

6 Claims, 9 Drawing Sheets

FIG. 2A

```
    ATGTGTCCCGCAAGCGCCTGGAGGAGGCCGCCCGGGCGCTGCCGGACGTGGTGGGATAAA
1   ------------+---------+---------+---------+---------+---------+ 60
     M  C  P  A  S  A  W  R  R  P  P  G  R  C  R  T  W  W  D  K
    GTGGAACGGGTGAGGGACATGTCTTGTGTGAATCAGCTGGACCCTTGGGATCCCAAACGT
61  ------------+---------+---------+---------+---------+---------+ 120
     V  E  R  V  R  D  M  S  C  V  N  Q  L  D  P  W  D  P  K  R
    TTGCCTGAGGAGAGTCCCTACTATTGGAAGGGAAGCCCCCAAGTGCTCAGAAGAAGCTCG
121 ------------+---------+---------+---------+---------+---------+ 180
     L  P  E  E  S  P  Y  Y  W  K  G  S  P  Q  V  L  R  R  S  S
    TTGCGCGACGAAGGGCGGCTTATTTTGGTTGACCTTTTCTCGGGGGCTGGGGGTTTCTCT
181 ------------+---------+---------+---------+---------+---------+ 240
     L  R  D  E  G  R  L  I  L  V  D  L  F  S  G  A  G  G  F  S
    GTGGGCTTTGAGCAAGCTGGCTTTGTGAGCGCTTTGGGCTTGGACATTTACACCGTTGCG
241 ------------+---------+---------+---------+---------+---------+ 300
     V  G  F  E  Q  A  G  F  V  S  A  L  G  L  D  I  Y  T  V  A
    GCCAAGACTTTCATGGAGCACCATCCGCGCGCAGGCTTCATTTTGGGGGATGCGCGTGCG
301 ------------+---------+---------+---------+---------+---------+ 360
     A  K  T  F  M  E  H  H  P  R  A  G  F  I  L  G  D  A  R  A
    GTGACCCCCGAGATGCTTTTGGAGGCGCTGAATGGTCTGCGCCCCCATGTGGTAACCGGA
361 ------------+---------+---------+---------+---------+---------+ 420
     V  T  P  E  M  L  L  E  A  L  N  G  L  R  P  H  V  V  T  G
    GGCGTTCCCTGCCAGCGCTTTTCCTTGACCAACAGAAAGCGAAATGATGAGGATCCCCGA
421 ------------+---------+---------+---------+---------+---------+ 480
     G  V  P  C  Q  R  F  S  L  T  N  R  K  R  N  D  E  D  P  R
    AACTACCTCTTTCGGGAGTTCATCCGGTTGGCTCGATTTCTCGATCCCGATGTGCTGATA
481 ------------+---------+---------+---------+---------+---------+ 540
     N  Y  L  F  R  E  F  I  R  L  A  R  F  L  D  P  D  V  L  I
    GTTGAGAACGTTTCAGGTATAAGATCGGCGGCCAACGGAAAGTTTGTCTTGGAAATCGTG
541 ------------+---------+---------+---------+---------+---------+ 600
     V  E  N  V  S  G  I  R  S  A  A  N  G  K  F  V  L  E  I  V
    CGCGCGATGGAGGAGGCGGGGTACAGGGCGCATGTGGAGGTGTTGAACGCTGCGGATTTT
601 ------------+---------+---------+---------+---------+---------+ 660
     R  A  M  E  E  A  G  Y  R  A  H  V  E  V  L  N  A  A  D  F
    GGGGTGCCACAGCACAGAAAGCGCATTTTCTTTGTTGGTGTCAGGCCGGGGATTGAGTTC
661 ------------+---------+---------+---------+---------+---------+ 720
     G  V  P  Q  H  R  K  R  I  F  F  V  G  V  R  P  G  I  E  F
    AGGTGGCCCCGACCGACGCATGGTCCCCTGGGAGAACATCCTTGGGTTTCTGTTTGGGAG
721 ------------+---------+---------+---------+---------+---------+ 780
     R  W  P  R  P  T  H  G  P  L  G  E  H  P  W  V  S  V  W  E
    GCCATAGGGGATCTTCCACCTCTAGGTCCTGGGGAATCTGCACACGAGTATCACCTCCCT
781 ------------+---------+---------+---------+---------+---------+ 840
     A  I  G  D  L  P  P  L  G  P  G  E  S  A  H  E  Y  H  L  P
    CCGCAAACGGATTATCAACGACGCATGAGGGAGGGCGCAGTTCTTCTCGGCAACCACGAG
841 ------------+---------+---------+---------+---------+---------+ 900
     P  Q  T  D  Y  Q  R  R  M  R  E  G  A  V  L  L  G  N  H  E
    AGTCCGAAGCATCCCAAGGGCACCTCTGAGATGATCGCAAACACCCCTCCAGGTGAACCT
901 ------------+---------+---------+---------+---------+---------+ 960
     S  P  K  H  P  K  G  T  S  E  M  I  A  N  T  P  P  G  E  P
    ATGTACGAGAAGTTTCGCCAGAGGATCCGTCTTCATCCCGATCGGCCGTCACCGACGATT
961 ------------+---------+---------+---------+---------+---------+ 1020
     M  Y  E  K  F  R  Q  R  I  R  L  H  P  D  R  P  S  P  T  I
```

FIG. 2B

```
     GTTGCTGGTGGTATTCGTCCGCAGTTTCAGTTTGGTCATCCCACGCAGCCTAGGGGACTC
1021 ---------+---------+---------+---------+---------+---------+ 1080
     V  A  G  G  I  R  P  Q  F  Q  F  G  H  P  T  Q  P  R  G  L
     ACCGTGAGGGAGCTGGCTCGGCTGCAGAGTTTCCCCGATGTGGTGTACTTTCATGGGGGC
1081 ---------+---------+---------+---------+---------+---------+ 1140
     T  V  R  E  L  A  R  L  Q  S  F  P  D  V  V  Y  F  H  G  G
     ATTGTTCAAGGGCGGGTGCAGACTGGGAACGCCGTGCCTCCTTTGATGGCAAGGGCCCTG
1141 ---------+---------+---------+---------+---------+---------+ 1200
     I  V  Q  G  R  V  Q  T  G  N  A  V  P  P  L  M  A  R  A  L
     GCGTTGGCGGTGAGGGCGGCTCTGGAGGACGGTTTTGATCCGGAGGAACACGGAGTGCCG
1201 ---------+---------+---------+---------+---------+---------+ 1260
     A  L  A  V  R  A  A  L  E  D  G  F  D  P  E  E  H  G  V  P
     CTTCGTAGCGCAGTTACTCGCGTGGCACTCTTCTGA
1261 ---------+---------+---------+------ 1296
     L  R  S  A  V  T  R  V  A  L  F  *
```

FIG. 3A

```
     ATGAAACGGAGCGAGATCGAGGAACTTCTAGAAATCTTCAGATGCAGTCTTCTCTCCATC
  1  ------------+---------+---------+---------+---------+---------+  60
      M  K  R  S  E  I  E  E  L  L  E  I  F  R  C  S  L  L  S  I
     CCATCAGGCCCATTCGCGAGGCGAGTTCACCAATTCACCCTCCACGGATACACTTATCCC
 61  ------------+---------+---------+---------+---------+---------+ 120
      P  S  G  P  F  A  R  R  V  H  Q  F  T  L  H  G  Y  T  Y  P
     TTTGTGGAGCAGTATGGAGAGGCTGCCCTGCCGGATCCTCCACCCGTGGAGGTAACAGGC
121  ------------+---------+---------+---------+---------+---------+ 180
      F  V  E  Q  Y  G  E  A  A  L  P  D  P  P  P  V  E  V  T  G
     CGCGCCTCCCGACGTCACTCCATGCTGGCAGCGGTACTTTTGGCGATGAAGGGTGACTTC
181  ------------+---------+---------+---------+---------+---------+ 240
      R  A  S  R  R  H  S  M  L  A  A  V  L  L  A  M  K  G  D  F
     CTCTTTTTCTTTCAAGCTGATCCACAAGATCCCGAGTTGGGGAGTCGAAGAGGCATCCGA
241  ------------+---------+---------+---------+---------+---------+ 300
      L  F  F  F  Q  A  D  P  Q  D  P  E  L  G  S  R  R  G  I  R
     GGAGTCTATACCGTTAAGGGCCCTCCCGGCCGGGCTGGGCACACGAAACCTCTGGAACAT
301  ------------+---------+---------+---------+---------+---------+ 360
      G  V  Y  T  V  K  G  P  P  G  R  A  G  H  T  K  P  L  E  H
     CCCCACTACGGAAAAGACTACAAAATGCATGCTGCTTGCCCTAAATGTGGGTCCCCATTC
361  ------------+---------+---------+---------+---------+---------+ 420
      P  H  Y  G  K  D  Y  K  M  H  A  A  C  P  K  C  G  S  P  F
     TCCAGCCTCTACGGCGCGTGCCCAGAGTGTGGGAATCCGTTGCCGTTGCCACCAAAACCC
421  ------------+---------+---------+---------+---------+---------+ 480
      S  S  L  Y  G  A  C  P  E  C  G  N  P  L  P  L  P  P  K  P
     TCACGCTTTTTGCGCAAAGGCAAAGAACCTCTCCCAGAACACGTCCTGAGCGTTCGCCTC
481  ------------+---------+---------+---------+---------+---------+ 540
      S  R  F  L  R  K  G  K  E  P  L  P  E  H  V  L  S  V  R  L
     CCCGTCGAACCCTTCACCGTCTTTGAAAGAGAGGTGACAGACGAGAGAGTCTATGGCGAC
541  ------------+---------+---------+---------+---------+---------+ 600
      P  V  E  P  F  T  V  F  E  R  E  V  T  D  E  R  V  Y  G  D
     ATGAGTTCCGACAACATCCTGGATCGAGCCCTCGTGTGGATTGGGCGCCACGACAACGCA
601  ------------+---------+---------+---------+---------+---------+ 660
      M  S  S  D  N  I  L  D  R  A  L  V  W  I  G  R  H  D  N  A
     ATGGGGGCAGGGAAAGGCAGCTCCGTGCGCCAACTCCTGCCGGAGGAGGCCCTGAGAATC
661  ------------+---------+---------+---------+---------+---------+ 720
      M  G  A  G  K  G  S  S  V  R  Q  L  L  P  E  E  A  L  R  I
     TACAAGCTTCTGCTTACGGAGTCGGATCAAAGGCTGAAGTCCCTCAGCTCACCCTCAGGG
721  ------------+---------+---------+---------+---------+---------+ 780
      Y  K  L  L  L  T  E  S  D  Q  R  L  K  S  L  S  S  P  S  G
     TTACCTACTGGCCACATCCCCATCCTAAATCCAGATGGAACCCCCCTGGAgTGCGTATTG
781  ------------+---------+---------+---------+---------+---------+ 840
      L  P  T  G  H  I  P  I  L  N  P  D  G  T  P  L  E  C  V  L
     ACAACAGAAGATTCGTCAAAGGTTAGAGAAGAAATTTCTATACACACCGCCcTATCCAAA
841  ------------+---------+---------+---------+---------+---------+ 900
      T  T  E  D  S  S  K  V  R  E  E  I  S  I  H  T  A  L  S  K
     GAAGTGAACAACCcTCATTCGTGCCTTTACAAAAGGCTAATCCCCAAGACCGTACCAGGA
901  ------------+---------+---------+---------+---------+---------+ 960
      E  V  N  N  P  H  S  C  L  Y  K  R  L  I  P  K  T  V  P  G
     TTACAGAACCTTTGGCAAACCCACTACTTAGAGTACGTCTCCTcTGAGTTTCCTTGGGGT
961  ------------+---------+---------+---------+---------+---------+ 1020
      L  Q  N  L  W  Q  T  H  Y  L  E  Y  V  S  S  E  F  P  W  G
```

FIG. 3B

```
     TACACCGGTTCCACCTCCGActACGTGCTCGTCTTCCGTCCTCGAGATGGGAGCCCGGTT
1021 ---------+---------+---------+---------+---------+---------+ 1080
     Y  T  G  S  T  S  D  Y  V  L  V  F  R  P  R  D  G  S  P  V
     CGGCACGCAGTCGTCATAGAGTTCAAAAGGGACGAGGTGGGCATTGCGGAAGTGATGCAG
1081 ---------+---------+---------+---------+---------+---------+ 1140
     R  H  A  V  V  I  E  F  K  R  D  E  V  G  I  A  E  V  M  Q
     GCTTGGcTTTACATGCCCTGGGTCGCCCAACTTTTGGGCATGCACTTGGGCAACCTCGTC
1141 ---------+---------+---------+---------+---------+---------+ 1200
     A  W  L  Y  M  P  W  V  A  Q  L  L  G  M  H  L  G  N  L  V
     GGTCAACCTGGGCGCCTCGTGGAGGTTCACTTAACACCGGTCCTTGTGGGAGCAAGACTG
1201 ---------+---------+---------+---------+---------+---------+ 1260
     G  Q  P  G  R  L  V  E  V  H  L  T  P  V  L  V  G  A  R  L
     GTGGGAAGAGGCCAAAACCGAATTCACGTTTTGCCCAGGGGTTATGACCGAACTGTGACG
1261 ---------+---------+---------+---------+---------+---------+ 1320
     V  G  R  G  Q  N  R  I  H  V  L  P  R  G  Y  D  R  T  V  T
     TACTACAACGGGGCTAAAGTCCGCCACGTTGTAAATCCCCCAGTTTTCTGGGAGTACAGC
1321 ---------+---------+---------+---------+---------+---------+ 1380
     Y  Y  N  G  A  K  V  R  H  V  V  N  P  P  V  F  W  E  Y  S
     TTGAAACCGTGTGGATCCAGTCAAAACAGAGCAGAAGTTAGGTTTTCACCAATTCATTTG
1381 ---------+---------+---------+---------+---------+---------+ 1440
     L  K  P  C  G  S  S  Q  N  R  A  E  V  R  F  S  P  I  H  L
     AACATCAAAACGATAAACTACATCCCACCAATAGGCACTTCCACAGCCGAAGCCGAGCGG
1441 ---------+---------+---------+---------+---------+---------+ 1500
     N  I  K  T  I  N  Y  I  P  P  I  G  T  S  T  A  E  A  E  R
     AATAGGGCAATAGAAGAGTTCAGGAGGCTCGCGAAAAGCCTCTCTATGGGAATCCCCCTC
1501 ---------+---------+---------+---------+---------+---------+ 1560
     N  R  A  I  E  E  F  R  R  L  A  K  S  L  S  M  G  I  P  L
     CTTTAA
1561 ------ 1566
     L  *
```

FIG. 4

```
    TTGATCCGGAGGAACACGGAGTGCCGCTTCGTAGCGCAGTTACTCGCGTGGCACTCTTCT
1   ------------+---------+---------+---------+---------+---------+ 60
    M  I  R  R  N  T  E  C  R  F  V  A  Q  L  L  A  W  H  S  S
    GACGCCCATCGTCGTGATGTCTTCTGGTGGAGGGGCGTTGAGGATCCCTATGTTCTTTTC
61  ------------+---------+---------+---------+---------+---------+ 120
    D  A  H  R  R  D  V  F  W  W  R  G  V  E  D  P  Y  V  L  F
    GTTGTTGAAGTGCTCTTGGCACGCACTCGCGCAGAGCGTGTGTCCGAAGTGGCGCGGGAA
121 ------------+---------+---------+---------+---------+---------+ 180
    V  V  E  V  L  L  A  R  T  R  A  E  R  V  S  E  V  A  R  E
    CTTGTGCAACGATGGCCCGAATTCTGCTCGCTTGCAAGAGCTGATGAGGCTGAGCTGGAG
181 ------------+---------+---------+---------+---------+---------+ 240
    L  V  Q  R  W  P  E  F  C  S  L  A  R  A  D  E  A  E  L  E
    CAGATGCTCCGACCTCTGGGTTTCCAAAGGGTTAGAGCTTCGGCTCTGAAGAGAGCGGCA
241 ------------+---------+---------+---------+---------+---------+ 300
    Q  M  L  R  P  L  G  F  Q  R  V  R  A  S  A  L  K  R  A  A
    GAGGAGGTCTGCACTCGGTGGGGGGGTAACCTGCCGCTTGAAGAGGAGAAGATTGCCTCT
301 ------------+---------+---------+---------+---------+---------+ 360
    E  E  V  C  T  R  W  G  G  N  L  P  L  E  E  E  K  I  A  S
    CTTCCAAGATCTGGCCGCTATGTGGCAAATGCAGTTTTGATTTACTCCACTTGTGCCAGG
361 ------------+---------+---------+---------+---------+---------+ 420
    L  P  R  S  G  R  Y  V  A  N  A  V  L  I  Y  S  T  C  A  R
    AAGGTGGCTGTTGACGTCAATGTGGCTCGTGTCGTCTCTCGCGTCTTTGGATTTATTTTA
421 ------------+---------+---------+---------+---------+---------+ 480
    K  V  A  V  D  V  N  V  A  R  V  V  S  R  V  F  G  F  I  L
    GTTAATGGAAAGGACCGGGAGGAGAACCTTTGGGCTCTGGCTCAACGTCTTGTTGAGTGC
481 ------------+---------+---------+---------+---------+---------+ 540
    V  N  G  K  D  R  E  E  N  L  W  A  L  A  Q  R  L  V  E  C
    ACATCTGGTTGCGAAGTGCGCAGTTTAAATTGGGCTCTTTTGGACGTTGGGCGCGAAATT
541 ------------+---------+---------+---------+---------+---------+ 600
    T  S  G  C  E  V  R  S  L  N  W  A  L  L  D  V  G  R  E  I
    TGTCACCCGACCAAACCTAGGTGTCCCCTTTGTCCCGTGCGTGAGATCTGCCACTTCGCG
601 ------------+---------+---------+---------+---------+---------+ 660
    C  H  P  T  K  P  R  C  P  L  C  P  V  R  E  I  C  H  F  A
    AGGTTCATCCGCATTTAG
661 ------------+------ 678
    R  F  I  R  I  *
```

US 6,589,769 B1

METHOD FOR CLONING AND EXPRESSION OF TSPRI RESTRICTION ENDONUCLEASE AND TSPRI METHYLASE IN E. COLI

BACKGROUND OF THE INVENTION

The present invention relates to recombinant DNA that encodes the TspRI restriction endonuclease (TspRI endonuclease or TspRI) as well as TspRI methyltransferase (TspRI methylase or M.TspRI), expression of TspRI endonuclease and methylase in E. coli cells containing the recombinant DNA.

TspRI endonuclease is found in the strain of Thermus species R (New England Biolabs' strain collection). It recognizes the double-stranded, palindromic DNA sequence 5' NNCASTGNN↓3' (SEQ ID NO:1) (S=C or G, ↓ indicates the cleavage position) and cleaves on both sides of the recognition sequence, generating a 9-base 3' overhang. TspRI methylase (M.TspRI) is also found in the same strain. It recognizes the double-stranded DNA sequence 5' CASTG 3' (SEQ ID NO:2) and presumably modifies the cytosine at the C5 position on hemi-methylated or non-methylated TspRI sites.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313 (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT↓AAA 3' (SEQ ID NO:3), 5' PuG↓GNCCPy 3' (SEQ ID NO:4) and 5' CACNNN↓GTG 3' (SEQ ID NO:5) respectively. *Escherichia coli* RY13, on the other hand, produces only one enzyme, EcoRI, which recognizes the sequence 5' G↓AATTC 3' (SEQ ID NO:6).

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into E. coli cloning vectors (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue" method, has been described for direct cloning of thermostable restriction endonuclease genes into E. coli based on the indicator strain of E. coli containing the dinD::lacZ fusion (Fomenkov et al., U.S. Pat. No. 5,498,535; Fomenkov et al., Nucl. Acids Res. 22:2399–2403, (1994)). This method utilizes the E. coli SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535, 1996). The disadvantage of this method is that some positive blue clones containing a restriction endonuclease gene are difficult to culture due to the lack of the cognate methylase gene.

There are three major groups of DNA methylases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5' CCWGG 3' (SEQ ID NO:7) (W=A or T) can also make the DNA resistant to PspGI restriction digestion. Another example is that CpM methylase can modify the C in CG dinucloetide and make the NotI site (5' GCGGCCGC 3' (SEQ ID NO:8)) refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest to obtain bacterial strains through recombinant DNA techniques that produce large quantities of restriction enzymes. Such over-expression strains should also simplify the task of enzyme purification.

SUMMARY OF THE INVENTION

The present invention relates to isolated DNA coding for the TspRI restriction endonuclease as well as to a method for cloning the TspRI restriction gene, tspRIR, from Thermus species R into *E. coli* by direct PCR from genomic DNA using degenerate primers based on the N-terminus and internal amino acid sequences.

It proved extremely difficult to clone TspRI endonuclease gene by conventional method. At first, a Sau3AI partial genomic DNA library was constructed. After TspRI digestion of the plasmids in the library, methylase positive clones were identified among the surviving transformants. The entire tspRIM gene was sequenced and adjacent DNA sequences beyond tspRIM gene were derived by inverse PCR. Four open reading frames (ORF1-ORF4) were found upstream and one ORF (ORF5) was found downstream. These ORFs were expressed in M.TspRI pre-modified host, but no TspRI activity was detected in cell extracts prepared from the clones with inserts of ORF1-ORF4 or ORF5.

Since methylase selection and inverse PCR cloning did not yield any TspRI positive clones, another cloning method, the "endo-blue" method was used to screen clones containing nuclease genes. More than 40 blue colonies were found from the Sau3AI partial library using the dinD: :lacZ indicator strain. However, no apparent TspRI endonuclease activity was detected in the cell extracts of blue colonies.

To find out whether TspRI methylase is a multi-specific methylase, the plasmid pUC-TspRIM was digested with many restriction enzymes that would be blocked by C5 methylation of their cognate C5 methylases. The plasmid pUC-TspRIM can be cleaved by all the restriction enzymes tested except TspRI endonuclease, suggesting that TspRI methylase is not a multi-specific methylase.

In order to obtain the N-terminus and internal amino acid sequences, major efforts were made to purify the native TspRI endonuclease to homogeneity. The successful cloning strategy was to design degenerate primers based on the N-terminus and internal amino acid sequences and to amplify TspRI coding sequence directly from genomic DNA by PCR. TspRI endonuclease was purified from the native strain Thermus cell extract by chromatography through Heparin hyper D, Source 15Q, Heparin tsk gel, Source 15S, Heparin tsk columns, and gel filtration column Sephadex 75. The purified homogeneous TspRI protein has an apparent molecular mass of 58 kDa, which was subjected to sequential degradation to obtain the N-terminus amino acid sequence. TspRI protein was also digested partially with CNBr, resulting three peptides with apparent molecular mass 6 kDa, 14 kDa, and 26 kDa. They were electro-blotted and sequenced to obtain the internal amino acid sequence of TspRI protein. Degenerate primers were made and a ~260 bp PCR product was found in a PCR reaction using a forward primer (designed from TspRI N-terminus amino acid sequence) and a reverse primer (designed from the internal 6 kDa amino acid sequence). The PCR product was cloned, sequenced and proved to be the bona fide N-terminal TspRI coding sequence. The C-terminus coding sequence of TspRI was identified from the partial ORF (355 bp) downstream of the putative T-G mismatch repair gene in that the predicted amino acid sequence matches the actual amino acid sequence of the CNBr-derived 14 kDa peptide. The entire tspRIR gene was amplified by PCR and ligated to a T7 expression vector pET21at and transformed into pre-modified expression host ER2566 [pACYC-TspRIM]. However, no desired insert was detected among the $Ap^R$ $Cm^R$ transformants. Therefore, the tspRIR gene was cloned and expressed in a low-copy-number T7 expression vector pACYC-T7ter. After clones with inserts were identified, the recombinant TspRI activity in cell extracts was detected by digestion of λ DNA. Both the tspRIR PCR product and the insert in pACYC-T7ter were sequenced and confirmed to encode the wild type amino acid sequence.

BRIEF DESCRIPTION OF THE DRAWINGS

FIG. 2. TspRI methylase gene sequence (tspRIM, 1296 bp (SEQ ID NO: 9)) and the encoded amino acid sequence (SEQ ID NO:10).

FIG. 3. TspRI endonuclease gene sequence (tspRIR, 1566 bp (SEQ ID NO:11)) and the encoded amino acid sequence (SEQ ID NO:12).

FIG. 4. T-G mismatch repair gene sequence (tmr gene,678 bp (SEQ ID NO:13)) and the encoded amino acid sequence (SEQ ID NO:14).

DETAILED DESCRIPTION OF THE INVENTION

The tspRIM gene was cloned by methylase selection from a Sau3AI partial genomic DNA library. However, cloning of tspRIR gene proved to be extremely difficult using conventional methods such as methylase selection, "endo-blue" or inverse PCR of adjacent DNA beyond the methylase gene.

Since R-M genes in a particular R-M system are usually located in close proximity to each other, initial efforts were made to clone the adjacent DNA sequences by inverse PCR.

In the first round of inverse PCR walking toward the upstream, an EagI PCR fragment was sequenced, generating ~700 bp of new sequence. In a second round of inverse PCR, an ApaI fragment PCR product was sequenced, giving rise to ~370 bp of new sequence upstream. A total of 1433 bp DNA was found before the methylase gene start codon, with ~1070 bp sequence derived by inverse PCR.

Figure 1:
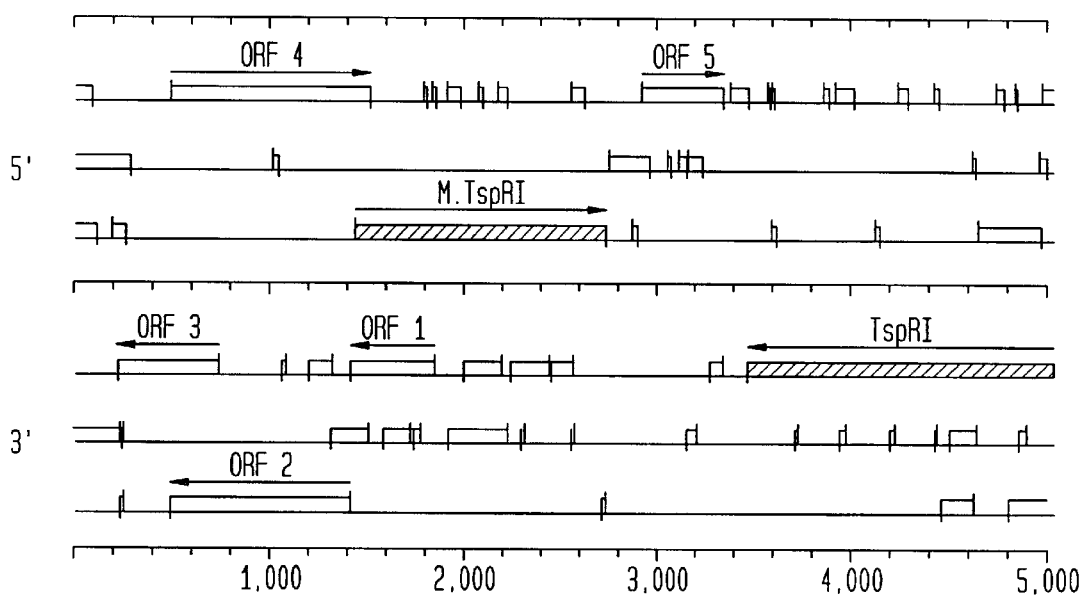
FIG. 1. TspRI restriction and modification system and adjacent open reading frames. Open reading frames 1–5 are shown as ORF1-ORF5. tspRIR, TspRI restriction endonuclease gene; tspRIM, TspRI methylase gene. ORF1 overlaps with tspRIM gene, ORF2, 3, and 4 are located upstream of tspRIM gene. ORF5, tmr gene, encoding the putative T-G mismatch repair protein.

Four ORFs were found in a segment of 1892 bp, part of which overlaps with tspRIM gene (see FIG. 1). The predicted amino acid sequences from ORF3 and ORF4 indicated that they have low homology to DNA metabolic enzymes (DNaseI, Integrase, and recombinase).

In order to express the four ORFs together in the same cell, ORF1 to ORF4 were amplified in PCR. Following restriction digestion with NdeI and HindIII, the PCR DNA was ligated to pET21a with compatible ends. The ligated DNA was transformed into pre-modified host ER2566 [pACYC-TspRIM]. Clones with PCR inserts were found and cell extracts prepared and assayed for TspRI activity. No restriction activity was detected. It was concluded that ORF1 to ORF4 do not encode TspRI endonuclease.

Since the upstream sequences (ORF1 to ORF4) did not yield any TspRI activity, efforts were directed to clone DNA sequence downstream of the M gene. PCR products were found in AatII, BsaHI, MspI, and RsaI templates. The PCR products were gel-purified and sequenced, generating 516 bp of new sequence downstream. One complete ORF (ORF5) and a partial ORF (ORF6, ~355 bp) were found. The predicted amino acid sequence from ORF5 has high homology to T-G mismatch DNA repair protein and endonuclease III. ORF5 was renamed as tmr gene (T-G mismatch repair), which is 675 bp, encoding a 225-amino acid protein with predicted molecular mass of 26 kDa. ORF5 was amplified by PCR and cloned into a low-copy-number T7 expression vector pACYC-T7ter and transformed into pre-modified host ER2566 [pBR-TspRIM]. Cell extracts were prepared and assayed for TspRI endonuclease activity. However, no apparent TspRI activity was detected. It was concluded that ORF5 (tmr gene) is not TspRI endonuclease gene.

Since methylase selection and inverse PCR cloning of DNA beyond M gene did not yield any positive results, an attempt was made to use the "endo-blue" method to clone nuclease genes from TspRI genomic DNA Sau3AI partial genomic DNA was ligated to BamHI-digested and CIP treated pUCl9 and the ligated DNA was used to transform *E. coli* indicator strain ER1992 (dinD::lacZ). The DNA damage inducible promoter was fused with lacZ and any DNA damage on the host genomic DNA will induce SOS response and also increase β-galactosidase expression. The colony turns blue on X-gal indicator plate if the colony contains a plasmid with nuclease gene insert. The nuclease gene can be non-specific endo/exo nuclease or type II restriction endonucleases. Forty blue colonies were identified and individual blue colony was amplified in 10 ml onvernight cultures and cell extracts prepared and assayed for restriction activity. No site-specific restriction activity was detected among 40 cell extracts.

There have been reports of multi-specific phage methylases that modify many restriction sites. For example, the BssHII phage methylase was shown to harbor at least five specificities (Schuman J. et al, (1996), J. Mol. Biol., 257:949–959). The phage-encoded methylases are usually orphan methylases that no endonucleases have been found next to them. To find out whether TspRI methylase is a multi-specific methylase, the plasmid pUC-TspRIM was digested with many restriction enzymes that would be blocked by C5 methylation of their cognate C5 methylases. However, the plasmid pUC-TspRIM can be cleaved by all the restriction enzymes tested except TSpRI endonuclease, indicating that TspRI methylase is not a multi-specific methylase.

The successful cloning strategy involved sequencing the native TspRI endonuclease protein to obtain the N-terminus and internal amino acid sequences. Degenerate PCR primers were used to amplify the coding sequence directly.

The preferred method described herein by which the TspRI methylase gene and the TspRI restriction endonuclease genes were cloned and expressed in *E. coli* included the following steps:

1. Genomic DNA Preparation and Genomic Library Construction

Genomic DNA was prepared from Thermus species R cells and digested partially with Sau3AI. The Sau3AI fragments were cloned into pUC19 vector with multiple TspRI sites. Approximately 30,000 $Ap^R$ transformants were amplified in 1 L culture and plasmid DNA prepared.

2. Cloning of tspRIM Gene by Methylase Selection

Varying amount of the plasmid library DNA was challenged with TspRI and the challenged DNA was transferred into ER2502 and ER2688 competent cells. Plasmid DNA was prepared from survivor transformants and screened for resistance to TspRI digestion. Two resistant clones were identified and the insert from one clone was completely sequenced. The sequence revealed that the TspRI methylase is a C5 methylase that shows extensive homology to other C5 methylases.

3. Subcloning of tspRIM Gene in pACYC184 and pBR322

In order to express tspRIM gene in *E. coli*, the tspRIM gene was amplified from the genomic DNA by PCR. The PCR DNA was purified, digested with SphI and SalI and ligated to pACYC184 or pBR322 with compatible ends. Plasmid pACYC-TspRIM showed partial resistance to TspRI digestion whereas plasmid pBR-TspRIM showed full resistance. The pre-modified hosts ER2566 [pACYC-TspRIM] and ER2566 [pBR-TspRIM] were used for expression of TspRI endonuclease.

4. Purification of TspRI Endonuclease from the Native Cells

TspRI endonuclease was purified to homogeneity from the native strain Thermus cell extract by chromatography through Heparin hyper D, Source 15Q, Heparin tsk gel, Source 15S, Heparin tsk columns, and gel filtration column Sephadex 75. The purified homogeneous TspRI protein has an apparent molecular mass of 58 kDa.

5. Protein Sequencing of TspRI Protein and Direct PCR of tspRIR Coding Sequence

The purified proteins were subjected to electrophoresis and electro-blotted to a membrane (Matsudaira,P., J.Biol. Chem., 262:10035–10038, (1987). Waite-Rees, P.A. et al. J. Bacteriology, 173:5207–5219, (1991)). The membrane was then stained with Commassie blue R-250 and the 58 kDa bands was excised and subjected to sequential degradation in an automated Precise 494 Protein/Peptide Sequencer (Applied Biosystems). A forward degenerate primer was designed from the N-terminus 8 amino acid residues (MKRSEIEE)

An additional sample of the TspRI endonuclease was treated with cyanogen bromide (CNBr). The partially digested peptides were subjected to electrophoresis and electro-blotted. The three major peptide bands 6 kDa, 14 kDa, and 26 kDa were cut out and subjected to sequential degradation.

The 6 kDa peptide contained the following amino acid sequence (SEQ ID NO:15):

KGDFLFFFQADPQDPELGSRRGIRGVYTVKG.

The amino acid sequence FFFQADPQDP (SEQ ID NO:16) was used to design PCR reverse primers. A ~260 bp PCR fragment was amplified in the PCR reaction which was blunted and ligated to HincII or SmaI digested and CIP treated pUC19. Clones with inserts were identified and sequenced. The DNA coding sequence was derived and translated into amino acid sequence which was compared to the actual amino acid sequence obtained by protein sequencing of the native purified TspRI protein. Among the N-terminus 33 amino acid residues, only two discrepancies were found. The inserts from multiple clones were sequenced and the accuracy of DNA and amino acid sequences were further confirmed.

6. Cloning of the Entire tspRIR Gene by PCR

There was a 355-bp partial ORF downstream of the T-G mismatch repair gene. The predicted amino acid sequence derived from the partial ORF matches perfectly with the amino acid sequence derived from the internal 14 kDa peptide of TspRI protein. It was concluded that the partial ORF was part of tspRIR gene, encoding the C-terminal part of the protein. Apparently, the TspRI R-M genes are not immediately next to each other. Instead, the R-M genes were separated from each other by a putative T-G mismatch repair gene.

7. Expression of tspRIR Gene in *E. coli*

So far, the N-terminal part coding sequence (~260 bp) and the C-terminal part coding sequence (355 bp) had been sequenced. In order to obtain the remaining coding sequence and to construct a stable expression clone, the strain ER2566 [pBR-TspRIM] was used as the expression host. It was difficult to express tspRIR gene in pET21at vector in the host ER2566 [pACYC-TspRIM], probably due to under-methylation of TspRI sites.

The tspRIR gene was amplified by PCR and the PCR product was completely sequenced to obtain the wild type reference sequence. It was also digested with NdeI and ligated to NdeI-cut and CIP treated pACYC-t7ter. The ligated DNA was used to transform ER2566 [pBR-TspRIM], selecting ApR and CmR colonies. Positive clones with the correct size insert and orientation were found. IPTG-induced cell extracts were prepared after 3 h of IPTG induction of late log phase 10 ml cell cultures. The cell extracts were assayed for TspRI activity on λ DNA. Four cell extracts display recombinant TspRI activity, with #6 and #17 displaying highest TspRI activity. The proteins in uninduced and IPTG-induced cell extracts were analyzed on SDS-PAGE and an induced protein band of approximately 58 kDa was detected in the IPTG-induced cell extract, but absent in the non-induced cell extract. The cell extracts were also heat-treated at 65° C. and 75° C. for 30 min and denatured proteins were removed by centrifugation at room temperature for 15 min. The clarified supernatant was then assayed for TspRI activity. Both samples displayed high TspRI activity at 65° C., indicating that like the native enzyme, the recombinant TspRI is also thermostable at 65° C. and 75° C.

The plasmid DNA pACYC-T7ter-TspRIR clone #17 was prepared by Qiagen tip-20 column and the entire insert was sequenced. It was found that the insert contained the wild type sequence except one base silent mutation that still encodes the wild type amino acid.

The present invention is further illustrated by the following Example. This Example is provided to aid in the understanding of the invention and is not construed as a limitation thereof.

The references cited above and below are herein incorporated by reference.

EXAMPLE 1

Cloning of TspRI Restriction-modification System in *E. coli*

1. Preparation of Genomic DNA

Genomic DNA was prepared from 4 g of Thermus species R (New England Biolabs collection) by the standard procedure consisting of the following steps:

(a) Cell lysis by addition of lysozyme (2 mg/ml final), sucrose (1% final), and 50 mM Tris-HCl, pH 8.0.
(b) Further cell lysis by addition of SDS at a final concentration of 0.1%.
(c) Further cell lysis by addition of 1% Triton X-100, 62 mM EDTA, 50 mM Tris-HCl, pH 8.0.
(d) Removal of proteins by phenol-$CHCl_3$ extraction of DNA 3 times (equal volume) and $CHCl_3$ extraction once.
(e) DNA dialysis in 4 liters of TE buffer, change 3 times.
(f) RNase A treatment to remove RNA, genomic DNA precipitation in 95% ethanol, centrifuged, washed, dried and resupended in TE buffer.

2. Restriction Digestion of Genomic DNA and Construction of Genomic DNA Library

Restriction enzyme Sau3AI was diluted by 2-fold serial dilutions (4, 2, 1, 0.5 units). Ten μg Thermus genomic DNA were digested partially with Sau3AI and partial digestion was achieved by 1 and 0.5 units of Sau3AI. The Sau3AI genomic fragments were ligated to BamHI digested and CIP treated pUCl9 vector that contains multiple TspRI sites. The ligated DNA was used to transform *E. coli* RR1 competent cells (ER2502, DnaseI) by electroporation. Approximately 30,000 $Ap^R$ transformants were obtained for the Sau3AI library. All the colonies were pooled and amplified in 1 liter LB+Ap overnight. Plasmid DNA was prepared by Qiagen Maxi-prep columns.

3. Cloning of TspRI Methylase Gene by Methylase Selection

Varying amount of the plasmid library DNA (0.25 μg, 0.5 μg, 1 μg) was challenged with TspRI for 2 h at 65° C. The TspRI-digested DNA was used to transform ER2502 and ER2688 competent cells. Plasmid DNA was prepared from 1.5 ml cell cultures inoculated from the transformants and screened for resistance to TspRI digestion. Eighteen plasmid mini-preparations were made and two plasmids were found to be resistant to TspRI digestion. The insert of two clones (#1 and #8) showed identical restriction patterns and the insert from #1 was completely sequenced using pUC universal primers, custom-made primers, and GPS insertion primers (NEB). The TspRI methylase is a C5 methylase that shows extensive homology to other C5 methylases. M.TspRI presumably methylates the C5 position of cytosine in the recognition sequence 5' NNCASTGNN 3' (S=C OR G) (SEQ ID NO:1) on hemi-methylated or non-methylated DNA.

4. Subcloning of tspRIM Gene in pACYC184 and pBR322

In order to express tspRIM gene in *E. coli*, two primers were made with the following sequences:

5' tcagcagcatgcggaggtttaaaaatgtgtcccgcaagcgcctggagg 3' (202–51, underlined bases=SphI site) (SEQ ID NO:17)

5' cgacgagtcgactcagaagagtgccacgcgagtaac 3' (202–40, underlined bases=SalI site) (SEQ ID NO:18)

The tspRIM gene was amplified from the genomic DNA using primers 202–51 and 202–40 under PCR condition of 950° C. 1 min, 600C 1 min, 720C 2 min for 20 cycles. The PCR DNA was purified by phenol-CH₃Cl extraction and CH₃Cl extraction, precipitated with ethanol, dried, and resuspended in TE buffer. Following restriction digestion with SphI and SalI and purification through Qiagen spin column, the PCR DNA was ligated to pACYC184 and pBR322 with compatible ends. After screening 18 Cm$^R$ transformants in pACYC, 15 clones contained tspRIM gene insert. However, all 15 pACYC-TspRIM plasmids showed partial resistance to TspRI digestion following 1.5 h incubation with TspRI endonuclease at 65° C. Eighteen AP$^R$ transformants in pBR322 were screened for inserts and their resistance to TspRI digestion. Three plasmids pBR-TspRIM (#4, #10, #11) showed full resistance to TspRI digestion. The premodified hosts ER2566 [pACYC-TspRIM] and ER2566 [pBR-TspRIM] were used for expression of TspRI endonuclease (see section 13, Expression of tspRIR gene in *E. coli*).

5. Cloning of DNA Upstream of TspRI Methylase

Since R-M genes in a particular R-M system are usually located in close proximity to each other, efforts were made to clone the upstream sequence.

Two primers were synthesized with the following sequences:

5' cggcccagcgggccctgcaccagt 3' (199–48) (SEQ ID NO:19)

5' gaggaccaccacccgctcctttcc 3' (199–49) (SEQ ID NO:20)

The genomic DNA was digested with AflIII, AluI, ApoI, AvrII, BamHI, BsaWI, BssHI, BstEII, EagI, HaeII, HhaI, HincII, NcoI, NlaIII, NsiI, NspI, PstI, PvuII, SacII, StyI, TfiI, and TseI, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. Five to 10 μl of the ligated products were used as the templates for inverse PCR. PCR conditions were 95° C. 30 sec, 60° C. 30 sec, 72° C. 2 min for 30 cycles. PCR products were found in EagI, HaeII, HhaI, NlaIII, PstI, and TfiI templates. The PCR DNA products were purified from a low-melting agarose gel and sequenced with primers 199–48 and 49. The entire EagI fragment was sequenced, generating ~700 bp of new sequence upstream.

A second set of inverse PCR primers were synthesized with the following sequences:

5' cgaatcttttgcgaatgctatact 3' (SEQ ID NO:21)

5' gagggaagcccagaccgaggaaga 3' (SEQ ID NO:22)

The genomic DNA was digested with ApaI, BsrFI, HaeII, HhaI, KpnI, NlaIII, SacI, Sau3AI, TaqI, and XhoI, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. Five to 10 μl of the ligated products were used as the template for inverse PCR. PCR conditions were 95° C. 30 sec, 55° C. 1 min, 72° C. 2 min for 30 cycles. PCR products were found in ApaI and Sau3AI templates. The PCR DNA products were purified from a low-melting agarose gel and sequenced with primers 205–54 and 55. The entire ApaI fragment was sequenced, generating ~370 bp of new sequence upstream.

A total of 1433 bp of DNA sequence was found upstream of the M gene in which four ORFs were found in a segment of 1892 bp, part of which overlaps with tspRIM gene. The predicted amino acid from ORF1 has less than 20% homology to a transcription factor. The predicted amino acid sequence from ORF2 shows 33% amino acid sequence identity to a collagen protein. ORF3 amino acid sequence demonstrated low homology to a human herpevirus DNase. ORF4 amino acid sequence has high homology to DNA integrase/invertase/recombinase.

6. Expression of Upstream Sequence (ORF1 to ORF4) in *E. coli*

In order to express these four ORFs (ORF1 to ORF4) together in the same cell, two PCR primers were made with the following sequences:

5' ctcatcatt<u>catatg</u>tctggtggtcaaggaaaagccgtg 3' (205–153, underlined bases=NdeI site) (SEQ ID NO:23)

5' gcttgggcc<u>aagcttt</u>tgatggtcagcaggagcttgcct 3' (206–119, underlined bases=HindIII site) (SEQ ID NO:24) 5 ORF1 to ORF4 were amplified in PCR using 205–153 and 206–119 under PCR condition of 95° C. 1 min, 60° C. 1 min, 72° C. 2 min for 20 cycles. The PCR DNA was purified by phenol-CH₃Cl extraction and CH₃Cl extraction, precipitated with ethanol, dried and resuspended in TE buffer. Following restriction digestion with NdeI and HindIII and purification through Qiagen spin column, the PCR DNA was ligated to pET21a with compatible ends. The ligated DNA was transformed into pre-modified host ER2566 [pACYC-TspRIM]. Clones with PCR inserts were found and ten cell extracts were prepared and assayed for TspRI endonuclease activity. The activity result was negative. It was concluded that ORF1 to ORF4 did not encode TspRI endonuclease.

7. Cloning of Downstream Sequence of tspRIM Gene

Since the upstream sequences (ORF1 to ORF4) did not yield any TspRI endonuclease activity, efforts were directed to clone DNA sequence downstream of the M gene. Inverse PCR primers were made with the following sequences:

5' gtgtcccctttgtcccgtgcgtg 3' (200–42) (SEQ ID NO:25)

5' ctaggtttggtcgggtgacaaatt 3' (200–43) (SEQ ID NO:26)

The genomic DNA was digested with AatII, ApoI, BsaHI, DraI, EaeI, EcoRI, FspI, HaeIII, MspI, RsaI, and Tsp509I, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. Five to 10 μl of the ligated products were used as the template for inverse PCR. PCR conditions were 95° C. 30 sec, 55° C. 1 min, 72° C. 2 min for 30 cycles. PCR products were found in AatII, BsaHI, MspI, and RsaI templates. The PCR DNA products were purified from a low-melting agarose gel and sequenced with primers 200–42 and 43, generating 516 bp of new sequence downstream. One complete ORF (ORF5) and a partial ORF (ORF6, ~355 bp) downstream of tspRIM were found. The predicted amino acid sequence from ORF5 has high homology to T-G mismatch DNA repair protein and endonuclease III. ORF5 was renamed as tmr gene (T-G mismatch repair), which is 675 bp, encoding a 225-amino acid protein with predicted molecular mass of 26 kDa. ORF5 was amplified by PCR and cloned into a low-copy-number T7 expression vector pACYC-T7ter and transformed into ER2566 and pre-modified host ER2566 [pBR-TspRIM]. Cell extracts were prepared and assayed for TspRI endonuclease activity. However, no apparent TspRI endonuclease activity was detected. It was concluded that ORF5 (tmr gene) is not TspRI endonuclease gene.

8. Attempt to Use "endo-blue" Method to Clone Nuclease Gene from TspRI Genomic DNA Sau3AI partial genomic DNA was ligated to BamHI-digested and CIP treated pUC19 and the ligated DNA was used to transform *E. coli* indicator strain ER1992 (dinD::lacZ). The DNA damage inducible promoter is fused with lacZ and any DNA damage on the host genomic DNA will induce SOS response and also increase β-galactosidase expression. The colony turns blue on X-gal indicator plate if the colony contains a plamid with nuclease gene insert. The nuclease gene can be non-specific endo/exo nuclease or type II restriction endonucleases. Forty blue colonies were identified from two transformation experiments. Individual blue colony was inoculated into 10 ml LB plus Ap and cultured overnight at 30° C. in a shaker. Cells was harvested by centrifugation and resupended in a sonication buffer (50 mM Tris-HCl, pH 7.8, 10 mM β-mercaptoethanol) and lysed by sonication. Five µl of Cell extracts was incubated with 1 µg λ DNA at 65° C. for one h and the digested DNA was then analyzed by agarose gel electrophoresis. No site-specific restriction endonuclease activity was detected among 40 cell extracts.

9. TspRI Methylase is a Mono-specific Methylase

There have been reports of multi-specific phage methylases that modify many restriction sites. For example, the BssHII phage methylase was shown to harbor at least five specificities (Schuman J. et al, (1996), J. Mol. Biol., 257:949–959). The phage-encoded methylases are usually orphan methylases that no endonucleases have been found next to them. To find out whether TspRI methylase is a multi-specific methylase, the plasmid pUC-TspRIM was digested with many restriction enzymes that would be blocked by C5 methylation via their cognate C5 methylases. Plasmid pUC-TspRIM was digested with the following restriction enzymes:

AciI, AclI, AluI, ApaI, ApaLI, AvaII, BanI, BbvI, BlpI, BsaAI, BsrFI, BssHII, EagI, HaeIII, HgaI, HhaI, HinPlI, HpaII, MspI, NspI, SacI, Sau96I, Sau3AI, TseI, and TspRI, respectively.

The digested DNA was then analyzed by agarose gel electrophoresis. The plasmid pUC-TspRIM can be cleaved by all the restriction enzymes tested except TspRI endonuclease, indicating that TspRI methylase is not a multi-specific methylase. This experiment demonstrated that TspRI methylase specificity does not overlap with the 24 enzymes tested here. Although it cannot be completely ruled out at this stage, TspRI methylase is not likely a prophage-encoded orphan multi-specific methylase.

10. Purification of TspRI Endonuclease from the Native Cells

Four hundred and ten grams of Thermus sp. R cells were resuspended in a 820 ml of SB buffer (20 mM KPO$_4$, pH 6.9, 0.1 mM EDTA, 7 mM β-mercaptoethanol) plus 0.1 M N$_a$Cl, 5% glycerol. Cell lysis was completed by passing through a Gaulin Press four times. Complete cell lysis was achieved by monitoring the maximum level of proteins released into the buffer. The clarified supernatant was loaded into a Heparin hyper D column (392 ml). After extensive washing with low salt SB buffer, the proteins were eluted with a salt gradient of 0.1–1 M N$_a$Cl in buffer SB plus 5% glycerol. Fractions were assayed for TspRI endonuclease activity on λ DNA. Active fractions 40 to 72 (~800 ml) were pooled and dialyzed against a TESH buffer (20 mM Tris-HCl, pH 8.0, 0.1 mM EDTA, 7 mM β-mercaptoethanol) plus 50 mM N$_a$Cl and 5% glycerol.

The dialyzed pool was loaded into a Source 15Q column (70 ml). TspRI endonuclease activity was found in the flow-through and washing fractions. Nevertheless, some contaminating proteins bound to the column and were separated from TspRI endonuclease. The active fractions were pooled and loaded into a Heparin tsk gel AF column (20 ml). After extensive washing with TESH buffer, proteins were eluted with a salt gradient of 50 mM to 1 M N$_a$Cl in TESH buffer plus 5% glycerol. TspRI endonuclease activity was identified in fractions 25–33, but only fractions 27 to 32 were pooled and diluted by the addition of SB buffer.

Figure 5:
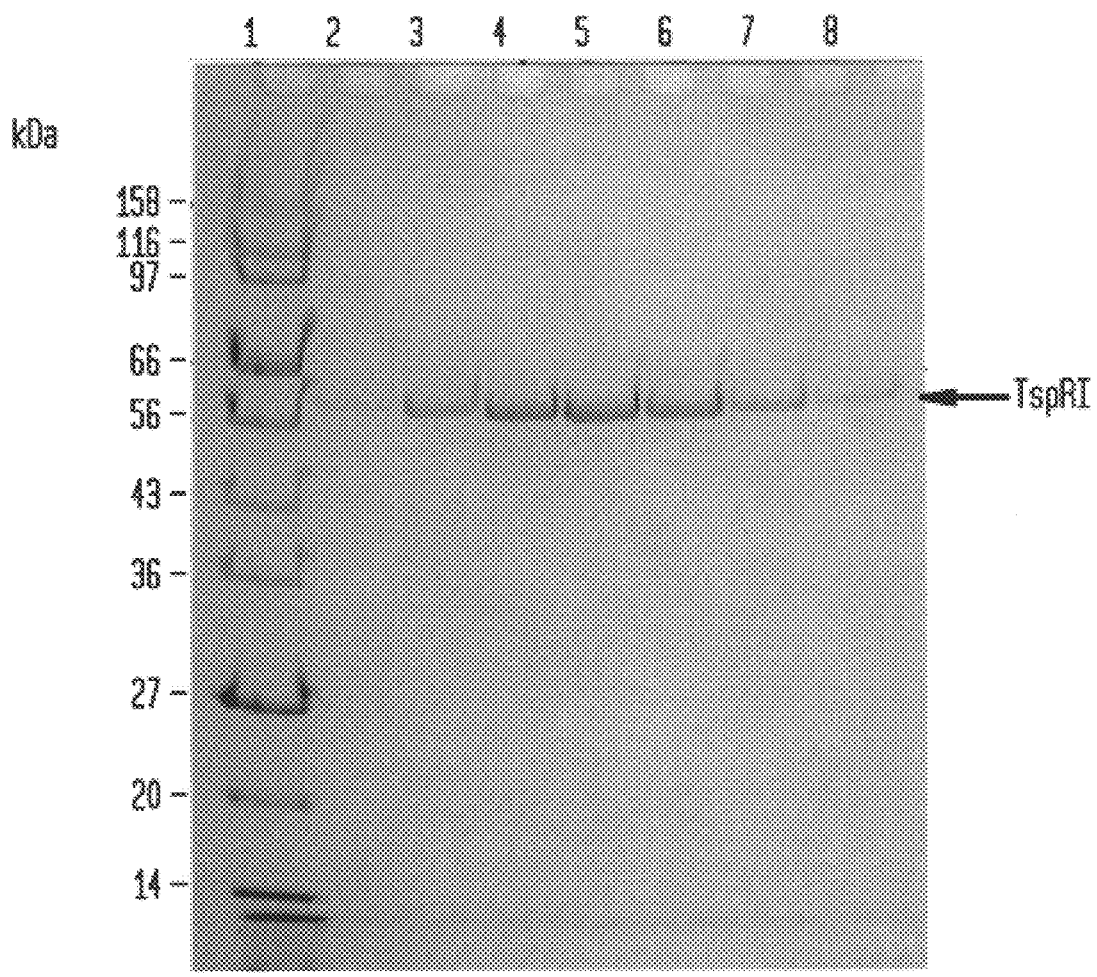
FIG. 5. SDS-PAGE analysis of the purified native TspRI endonuclease protein. Lane 1, protein size marker, lanes 2 to 8, purified TspRI protein.
Figure 6:
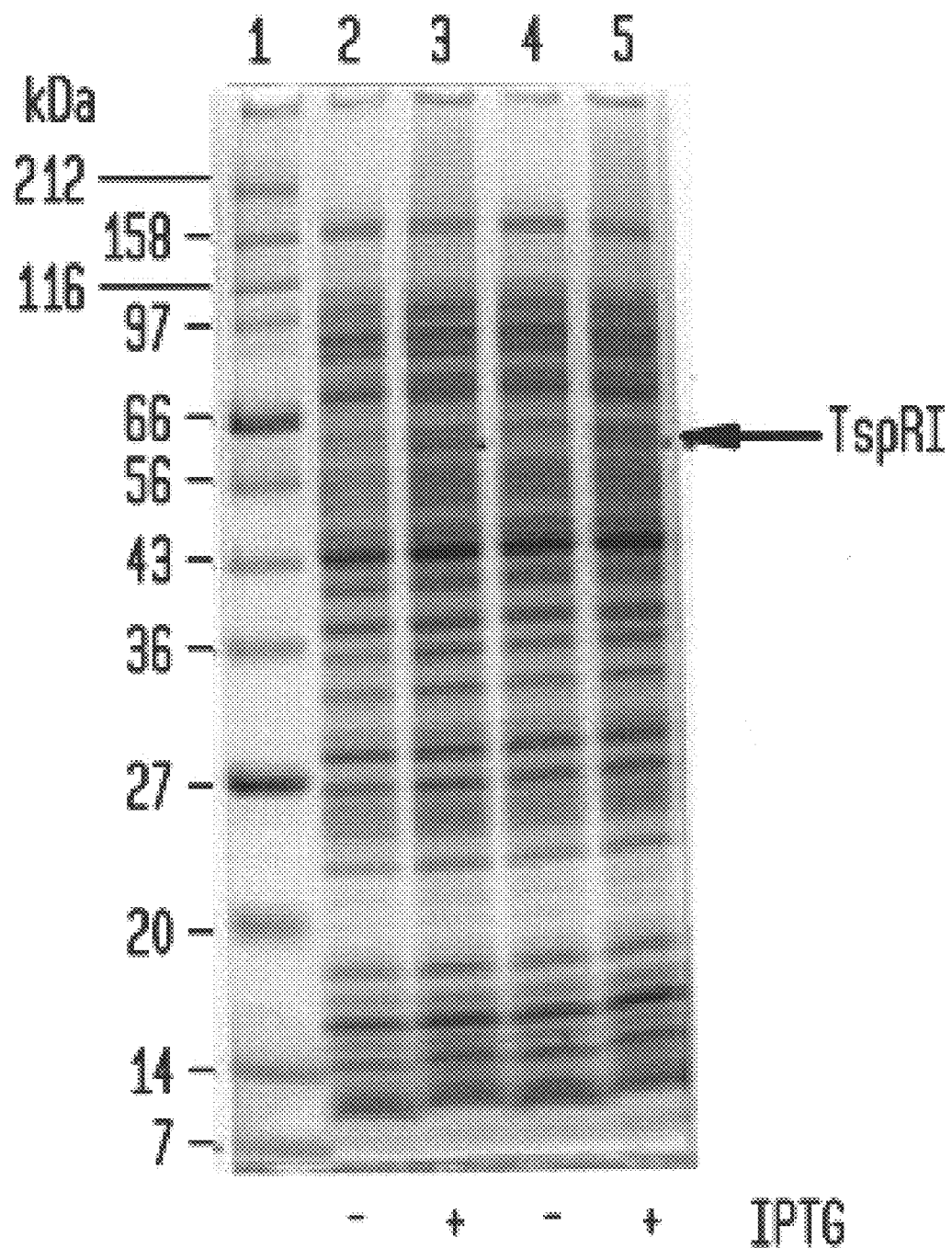
FIG. 6. Protein expression profiles of TspRI-producing clones on SDS-PAG gel. Lane 1, protein size marker; lanes 2 and 4, non-induced cell extract; lanes 3 and 5, IPTG-induced cell extract.
Figure 7:
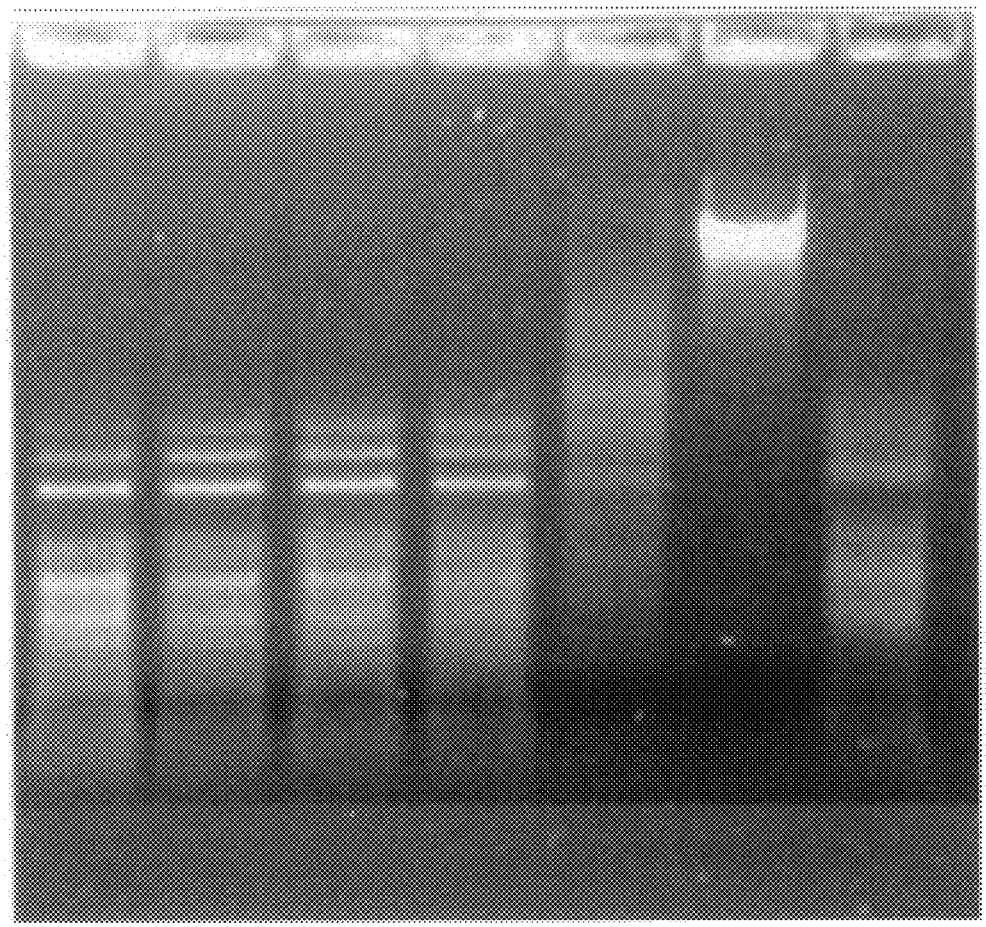
FIG. 7. Recombinant TspRI endonuclease activity in cell extract. Lanes 1 to 5, λ DNA incubated with diluted cell extract containing recombinant TSpRI. The dilution factors in lanes 1 to 5 were: 1/10, 1/30, 1/50, 1/100, 1/1000. Lane 6, λ DNA; lane 7, λ DNA digested with native TspRI.

The proteins were loaded into a Resource 15S column. Some TspRI protein bound to the column and was eluted with a salt gradient of 50 mM to 1 M N$_a$Cl in SB buffer plus 5% glycerol. The eluted active fractions 11–13 were pooled and dialyzed against a storage buffer (0.2 M NaCl, 20 mM Tris-HCl, pH 7.4, 0.1 mM EDTA, 1 mM DTT, 50% glycerol). This preparation was called purified TspRI "pool 1" which contained 1–1.2 million units of TspRI. During the chromatography using Resource 15S column, some TspRI activity was detected in the flow-through fractions. These fractions were pooled and loaded into a Heparin tsk column (AF HR 10/10) using SB buffer. After washing, TspRI protein was eluted with a salt gradient of 50 mM to 1 M N$_a$Cl in SB buffer plus 5% glycerol. The active fractions 27–29 were identified and pooled and dialyzed in a storage buffer. This preparation was called TspRI "pool 2" which contained about 0.9 million units of TspRI endonuclease. SDS-PAGE analysis of the proteins in "pool 2" indicated that there was a major protein band of 58 kDa TspRI protein. However, there were still two minor contaminating proteins (~12 and ~17 kDa, respectively). They were removed by chromatography through a Sephadex 75 column. Proteins were eluted in TESH buffer plus 0.5 M NaCl and 5% glycerol. Fraction 14–24 contained the homogeneous TspRI protein (FIG. 5). TspRI protein in fraction 18 was used for protein sequencing.

11. Amino Acid Sequence Analysis of TSPRI Endonuclease

The purified proteins were subjected to electrophoresis and electro-blotted to a membrane (Matsudaira P., J. Biol. Chem., 262:10035–10038, (1987). Waite-Rees P.A. et al., J. Bacteriology, 173:5207–5219, (1991). The membrane was then stained with Commassie blue R-250 and the 58 kDa bands was excised and subjected to sequential degradation in an automated Precise 494 Protein/Peptide Sequrncer (Applied Biosystems). The 58 kDa protein contained the following N-terminal amino acid sequence:

MKRSEIEELLEIFRxSLLSIPSGdF(x)RRVHQFT
(x=unknown amino acid, d=erroneous calling, (x)= omitted amino acid calling) (SEQ ID NO:27)

Arg and Ser codons are very degenerate. To reduce the degeneracy, four forward PCR primers were made based on the amino acid sequence MKRSEIEE (SEQ ID NO:28).

Primer 5' cgcggatccatgaaragrtcngaratcgarga 3' (234–276) (SEQ ID NO:29)

Protein MKRSEIEE (SEQ ID NO:28)

Primer 5' cgcggatccatgaarcgg↓lctcngaratcgarga 3' (234–277) (SEQ ID NO:30)

Primer 5' cgcggatccatgaaragragygaratcgarga 3' (234–278) (SEQ ID NO:31)

Primer 5' cgcggatccatgaarcgg↓cagygaratcgarga 3' (234–279) (SEQ ID NO:32)

The reverse PCR primer was made based on the following amino acid sequence: PSGdFRR (SEQ ID NO:33)

5' cgncgraartcnccrctngg 3' (237–95) (SEQ ID NO:34)

(The complementary sequence of 5' ccntcnggngayt tycgncg 3' (SEQ ID NO:35)).

Four sets of PCR reactions were set up using primers 234–276 and 237–95; 234–277 and 237–95; 234–278 and 237–95; 234–279 and 237–95, respectively. PCR conditions were 95° C. 5 min for 1 cycle, 95° C. 1 min, 40° C. 1 min, 72° C. 30 sec for 35 cycles. PCR products between 72 to 86 bp were gel purified and sequenced using the forward and reverse primers. No readable sequence was obtained, partly because of possible mixed PCR products or random-amplified products. The failure to amplify the N-terminus 80 bp coding sequence was probably due to the reverse primer that based on the erroneous amino acid calling. Later (described in section 12) it was discovered that the amino acid sequence PSGdFRR (SEQ ID NO:36) used for reverse primer design contained two mis-callings. The correct amino acid sequence should be: PSGPFARR (SEQ ID NO:37).

12. Amino Acid Sequencing of CNBr-derived Fragments of TspRI Protein

An additional sample of the TspRI endonuclease, 5 μg in 20 μl, was treated with 1 μg of cyanogen bromide (CNBr, Sigma) dissolved in 200 μl of 88% distilled formic acid for 24 hours in the dark at room temperature. This reaction mixture was evaporated to dryness and the sample was resuspended in 100 μl of SDS-PAGE loading buffer and subjected to electrophoresis and western blotted to PVDF. The three major peptide bands 6 kDa, 14 kDa, and 26 kDa were cut out and subjected to sequential degradation.

The 6 kDa peptide contained the following amino acid sequence:

KGDFLFFFQADPQDPELGSRRGIRGVYTVKG (SEQ ID NO:38)

The amino acid sequence FFFQADPQDP (SEQ ID NO:39) was used to design reverse primers for PCR.

The 14 kDa peptide contained the following amino acid sequence:

HLGNLVGQPGRLVEVHLTPVLVGAR-LVGRGQNRIHVLPRGYDRTVxYYN (x=unknown amino acid (SEQ ID NO:40))

The 26 kDa peptide contained the following amino acid sequence:

MGAGKGSSVRQLLPEEALGIYK (SEQ ID NO:41)

Two reverse PCR primers were made based on the 6 kDa amino acid sequence:

5' ggrtcytgnggrtcngcytg 3' (249–198) (SEQ ID NO:42)

5' ggrtcngcytgraaraaraa 3' (249–199) (SEQ ID NO:43)

Four PCR reactions were set up using primers 234–277 (F) and 249–198 (R); 234–277 (F) and 249–199 (R); 234–279 (F) and 249–198 (R); 234–279 (F) and 249–199 (R); (F=forward primer, R=reverse primer). A ~260 bp PCR fragment was found in the PCR reaction of 234–279 and 249–199 under PCR conditions of 95° C. 5 min for 1 cycle, 95° C. 1 min, 40° C. 1 min, 72° C. 2 min for 25 cycles. The PCR product was blunted by treatment with T4 polynucleotide kinase in the presence of ATP and ligated to HincII or SmaI digested and CIP treated pUC19. The ligated DNA was used to transform ER2688 and plated on LB agar, X-gal, Ap plates. After screening 18 white colonies, clones with PCR insert were identified and sequenced with pUC universal primers. The DNA coding sequence was derived and translated into amino acid sequence which was compared to the actual amino acid sequence obtained by protein sequencing of the native purified TspRI protein. Among the N-terminus 33 amino acid residues, only two discrepancies were found. The inserts from multiple active TspRI clones were sequenced and the correct DNA and amino acid sequences were further confirmed. The correct N-terminus amino acid sequence of TSpRI is as follows:

MKRSEIEELLEIFRCSLLSIPSGPFARRVHQFT (SEQ ID NO:44) (bold and underlined residues, different from the original amino acid sequence derived from the native protein)

There was a 355-bp partial ORF downstream of the T-G mismatch repair gene. The predicted amino acid sequence derived from the partial ORF matches perfectly with the amino acid sequence derived from the internal 14 kDa peptide. It was concluded that the partial ORF was part of tspRIR gene, encoding the C-terminus part of the protein. Apparently, the TspRI R-M genes are not immediately next to each other. Instead, they were separated from each other by a T-G mismatch repair gene.

13. Expression of tspRIR Gene in *E. coli*

So far, the N-terminal part coding sequence (~260 bp) and the C-terminal part coding sequence (355 bp) had been sequenced. In order to obtain the remaining coding sequence, two PCR primers were made with following sequences:

5' cgcggatccc<u>catatg</u>aaacggagcgagatcgaggaacttctagaa 3' (250–102, underlined bases, NdeI site) (SEQ ID NO:45)

5' tgggtcgacg<u>agctc</u>ttaaaggaggggattcccatagagag 3' (250–287, underlined bases, SacI site) (SEQ ID NO:46)

The tspRIR gene was amplified by PCR using primers 250–102 and 250–287 under PCR conditions of 95° C. 2 min for 1 cycle, 95° C. 1 min, 60° C. 1 min, 72° C. 2 min for 20 cycles. PCR product was digested with NdeI and SacI and gel-purified from a low-melting agarose gel. It was ligated to the T7 expression vector pET21at with compatible ends and the ligated DNA was used to transform ER2566 [pACYC-TspRIM]. After screening 18 transformants, no correct size insert was found. The failure to find the positive clones was probably due to the under-methylation of TspRI sites on the choromosomal DNA because tspRIM gene was expressed from a low-copy-number plasmid. In order to construct a stable expression clone, the tspRIM gene was cloned in pBR322 first and the strain ER2566 [pBR-TspRIM] used as the pre-modified host. This cloning strategy proved to be successful. Two new primers were made for PCR of tspRIR gene:

5' tggccccac<u>catatg</u>ttaaaggaggggattcccatagagag 3' (253–90, underlined bases=NdeI site) (SEQ ID NO:47)

5' cgcgtaggc<u>catatg</u>aaacggagcgagatcgaggaacttcta 3' (253–91, underlined bases=NdeI site) (SEQ ID NO:48)

The tspRIR gene was amplified by PCR using primers 253–90 and 253–91, 2 units of Vent DNA polymerase under PCR conditions of 95° C. 2 min for 1 cycle, 95° C. 1 min, 60° C. 1 min, 72° C. 2 min for 22 cycles (3 to 5 mM MgSO$_4$) PCR product was digested with NdeI and ligated to NdeI-cut and CIP treated pACYC-t7ter. The ligation condition was 0.2 μg pACYC-T7ter, 0.5 μg PCR DNA (tspRIR gene), 3 μl 10×ligation buffer, 1200 units T4 DNA ligase, sdH$_2$O to 30 μl at 16° C. overnight. The ligated DNA was used to transform ER2566 [pBR-TspRIM]. After screening 36 Ap$^R$ Cm$^R$ transformants, 7 positive clones with the correct size insert were found. IPTG-induced cell extracts were prepared after 3 h of IPTG induction of late log phase 10 ml cell cultures. The cell extracts were assayed for TspRI activity on λ DNA. Four cell extracts display recombinant TspRI activity, with #6 and #17 displaying highest TspRI activity. The proteins in uninduced and IPTG-induced cell extracts were analyzed on SDS-PAGE and an induced protein band of approximately 58 kDa was detected in the IPTG-induced cell extract, but absent in the non-induced cell extract. The cell extracts were also heat-treated at 65° C. and 75° C. for 30 min and denatured proteins were removed by centrifugation at room temperature for 15 min. The clarified supernatant was then assayed for TspRI activity. Both samples displayed high TspRI activity at 65° C., indicating that like the native enzyme, the recombinant TspRI is also thermostable at 65° C. and 75° C.

The plasmid DNA pACYC-T7ter-TspRIR clone #17 was prepared by Qiagen column tip-20 and the entire insert was sequenced. It was found that the insert contained the wild type sequence except one base silent mutation that still encodes the wild type amino acid.

The strain NEB#1346, ER2566 [pBR-TspRIM, pACYC-T7ter-TspRI] has been deposited under the terms and conditions of the Budapest Treaty with the American Type Culture Collection on Oct. 11, 2001 and received ATCC Accession No. PTA-3779.

What is claimed is:

1. Isolated DNA coding for the TspRI restriction endonuclease, wherein the isolated DNA is obtainable from ATCC No. PTA-3779.

2. A recombinant DNA vector comprising a vector into which a DNA segment encoding the TspRI restriction endonuclease has been inserted.

3. Isolated DNA encoding the TspRI restriction endonuclease and TspRI methylase, wherein the isolated DNA is obtainable from ATCC No. PTA-3779.

4. A vector which comprises the isolated DNA of claim 3.

5. A host cell transformed by the vector of claim 2 or 4.

6. A method of producing recombinant TspRI restriction endonuclease comprising culturing a host cell transformed with the vector of claim 2 or 4 under conditions suitable for expression of said endonuclease and methylase.

* * * * *

SEQUENCE LISTING

```
<160> NUMBER OF SEQ ID NOS: 48

<210> SEQ ID NO 1
<211> LENGTH: 9
<212> TYPE: DNA
<213> ORGANISM: Thermus sp. R
<220> FEATURE:
<221> NAME/KEY: misc_feature
<222> LOCATION: (1)..(2)
<223> OTHER INFORMATION: N=G, A, C or T
<220> FEATURE:
<221> NAME/KEY: misc_feature
<222> LOCATION: (8)..(9)
<223> OTHER INFORMATION: N=G, A, C or T
<220> FEATURE:
<221> NAME/KEY: misc_feature
<222> LOCATION: (5)..(5)
<223> OTHER INFORMATION: S=C or G

<400> SEQUENCE: 1 nncastgnn                                                                 9

<210> SEQ ID NO 2
<211> LENGTH: 5
<212> TYPE: DNA
<213> ORGANISM: Thermus sp. R
<220> FEATURE:
<221> NAME/KEY: misc_feature
<222> LOCATION: (3)..(3)
<223> OTHER INFORMATION: S=C or G

<400> SEQUENCE: 2 castg                                                                     5

<210> SEQ ID NO 3
<211> LENGTH: 6
<212> TYPE: DNA
<213> ORGANISM: Deinococcus radiophilus

<400> SEQUENCE: 3 tttaaa                                                                    6

<210> SEQ ID NO 4
<211> LENGTH: 5
<212> TYPE: DNA
<213> ORGANISM: Deinococcus radiophilus
<220> FEATURE:
<221> NAME/KEY: misc_feature
<222> LOCATION: (3)..(3)
<223> OTHER INFORMATION: N=G, A, C or T

<400> SEQUENCE: 4 ggncc                                                                     5

<210> SEQ ID NO 5
<211> LENGTH: 9
<212> TYPE: DNA
<213> ORGANISM: Deinococcus radiophilus
<220> FEATURE:
<221> NAME/KEY: misc_feature
<222> LOCATION: (4)..(6)
```

<223> OTHER INFORMATION: N=G, A, C or T

<400> SEQUENCE: 5 cacnnngtg                                                                          9

<210> SEQ ID NO 6
<211> LENGTH: 6
<212> TYPE: DNA
<213> ORGANISM: Escherichia coli

<400> SEQUENCE: 6 gaattc                                                                             6

<210> SEQ ID NO 7
<211> LENGTH: 5
<212> TYPE: DNA
<213> ORGANISM: Escherichia coli
<220> FEATURE:
<221> NAME/KEY: misc_feature
<222> LOCATION: (3)..(3)
<223> OTHER INFORMATION: W=A or T

<400> SEQUENCE: 7 ccwgg                                                                              5

<210> SEQ ID NO 8
<211> LENGTH: 8
<212> TYPE: DNA
<213> ORGANISM: Nocardia otitidis-caviarum

<400> SEQUENCE: 8 gcggccgc                                                                           8

<210> SEQ ID NO 9
<211> LENGTH: 1296
<212> TYPE: DNA
<213> ORGANISM: Thermus sp. R
<220> FEATURE:
<221> NAME/KEY: CDS
<222> LOCATION: (1)..(1296)
<223> OTHER INFORMATION:

<400> SEQUENCE: 9

| atg | tgt | ccc | gca | agc | gcc | tgg | agg | agg | ccg | ccc | ggg | cgc | tgc | cgg | acg | 48 |
|-----|-----|-----|-----|-----|-----|-----|-----|-----|-----|-----|-----|-----|-----|-----|-----|----|
| Met | Cys | Pro | Ala | Ser | Ala | Trp | Arg | Arg | Pro | Pro | Gly | Arg | Cys | Arg | Thr |    |
| 1   |     |     |     | 5   |     |     |     |     | 10  |     |     |     |     | 15  |     |    |

| tgg | tgg | gat | aaa | gtg | gaa | cgg | gtg | agg | gac | atg | tct | tgt | gtg | aat | cag | 96 |
|-----|-----|-----|-----|-----|-----|-----|-----|-----|-----|-----|-----|-----|-----|-----|-----|----|
| Trp | Trp | Asp | Lys | Val | Glu | Arg | Val | Arg | Asp | Met | Ser | Cys | Val | Asn | Gln |    |
|     |     |     | 20  |     |     |     |     | 25  |     |     |     |     | 30  |     |     |    |

| ctg | gac | cct | tgg | gat | ccc | aaa | cgt | ttg | cct | gag | gag | agt | ccc | tac | tat | 144 |
|-----|-----|-----|-----|-----|-----|-----|-----|-----|-----|-----|-----|-----|-----|-----|-----|-----|
| Leu | Asp | Pro | Trp | Asp | Pro | Lys | Arg | Leu | Pro | Glu | Glu | Ser | Pro | Tyr | Tyr |     |
|     |     |     | 35  |     |     |     |     | 40  |     |     |     |     | 45  |     |     |     |

| tgg | aag | gga | agc | ccc | caa | gtg | ctc | aga | aga | agc | tcg | ttg | cgc | gac | gaa | 192 |
|-----|-----|-----|-----|-----|-----|-----|-----|-----|-----|-----|-----|-----|-----|-----|-----|-----|
| Trp | Lys | Gly | Ser | Pro | Gln | Val | Leu | Arg | Arg | Ser | Ser | Leu | Arg | Asp | Glu |     |
| 50  |     |     |     |     | 55  |     |     |     |     | 60  |     |     |     |     |     |     |

| ggg | cgg | ctt | att | ttg | gtt | gac | ctt | ttc | tcg | ggg | gct | ggg | ggt | ttc | tct | 240 |
|-----|-----|-----|-----|-----|-----|-----|-----|-----|-----|-----|-----|-----|-----|-----|-----|-----|
| Gly | Arg | Leu | Ile | Leu | Val | Asp | Leu | Phe | Ser | Gly | Ala | Gly | Gly | Phe | Ser |     |
| 65  |     |     |     |     | 70  |     |     |     |     | 75  |     |     |     |     | 80  |     |

| gtg | ggc | ttt | gag | caa | gct | ggc | ttt | gtg | agc | gct | ttg | ggc | ttg | gac | att | 288 |
|-----|-----|-----|-----|-----|-----|-----|-----|-----|-----|-----|-----|-----|-----|-----|-----|-----|
| Val | Gly | Phe | Glu | Gln | Ala | Gly | Phe | Val | Ser | Ala | Leu | Gly | Leu | Asp | Ile |     |
|     |     |     |     | 85  |     |     |     |     | 90  |     |     |     |     | 95  |     |     |

| tac | acc | gtt | gcg | gcc | aag | act | ttc | atg | gag | cac | cat | ccg | cgc | gca | ggc | 336 |
|-----|-----|-----|-----|-----|-----|-----|-----|-----|-----|-----|-----|-----|-----|-----|-----|-----|
| Tyr | Thr | Val | Ala | Ala | Lys | Thr | Phe | Met | Glu | His | His | Pro | Arg | Ala | Gly |     |
|     |     |     | 100 |     |     |     |     | 105 |     |     |     |     | 110 |     |     |     |

```
ttc att ttg ggg gat gcg cgt gcg gtg acc ccc gag atg ctt ttg gag     384
Phe Ile Leu Gly Asp Ala Arg Ala Val Thr Pro Glu Met Leu Leu Glu
            115                 120                 125 gcg ctg aat ggt ctg cgc ccc cat gtg gta acc gga ggc gtt ccc tgc     432
Ala Leu Asn Gly Leu Arg Pro His Val Val Thr Gly Gly Val Pro Cys
130                 135                 140 cag cgc ttt tcc ttg acc aac aga aag cga aat gat gag gat ccc cga     480
Gln Arg Phe Ser Leu Thr Asn Arg Lys Arg Asn Asp Glu Asp Pro Arg
145                 150                 155                 160 aac tac ctc ttt cgg gag ttc atc cgg ttg gct cga ttt ctc gat ccc     528
Asn Tyr Leu Phe Arg Glu Phe Ile Arg Leu Ala Arg Phe Leu Asp Pro
                165                 170                 175 gat gtg ctg ata gtt gag aac gtt tca ggt ata aga tcg gcg gcc aac     576
Asp Val Leu Ile Val Glu Asn Val Ser Gly Ile Arg Ser Ala Ala Asn
            180                 185                 190 gga aag ttt gtc ttg gaa atc gtg cgc gcg atg gag gag gcg ggg tac     624
Gly Lys Phe Val Leu Glu Ile Val Arg Ala Met Glu Glu Ala Gly Tyr
        195                 200                 205 agg gcg cat gtg gag gtg ttg aac gct gcg gat ttt ggg gtg cca cag     672
Arg Ala His Val Glu Val Leu Asn Ala Ala Asp Phe Gly Val Pro Gln
    210                 215                 220 cac aga aag cgc att ttc ttt gtt ggt gtc agg ccg ggg att gag ttc     720
His Arg Lys Arg Ile Phe Phe Val Gly Val Arg Pro Gly Ile Glu Phe
225                 230                 235                 240 agg tgg ccc cga ccg acg cat ggt ccc ctg gga gaa cat cct tgg gtt     768
Arg Trp Pro Arg Pro Thr His Gly Pro Leu Gly Glu His Pro Trp Val
                245                 250                 255 tct gtt tgg gag gcc ata ggg gat ctt cca cct cta ggt cct ggg gaa     816
Ser Val Trp Glu Ala Ile Gly Asp Leu Pro Pro Leu Gly Pro Gly Glu
            260                 265                 270 tct gca cac gag tat cac ctc cct ccg caa acg gat tat caa cga cgc     864
Ser Ala His Glu Tyr His Leu Pro Pro Gln Thr Asp Tyr Gln Arg Arg
        275                 280                 285 atg agg gag ggc gca gtt ctt ctc ggc aac cac gag agt ccg aag cat     912
Met Arg Glu Gly Ala Val Leu Leu Gly Asn His Glu Ser Pro Lys His
    290                 295                 300 ccc aag ggc acc tct gag atg atc gca aac acc cct cca ggt gaa cct     960
Pro Lys Gly Thr Ser Glu Met Ile Ala Asn Thr Pro Pro Gly Glu Pro
305                 310                 315                 320 atg tac gag aag ttt cgc cag agg atc cgt ctt cat ccc gat cgg ccg    1008
Met Tyr Glu Lys Phe Arg Gln Arg Ile Arg Leu His Pro Asp Arg Pro
                325                 330                 335 tca ccg acg att gtt gct ggt ggt att cgt ccg cag ttt cag ttt ggt    1056
Ser Pro Thr Ile Val Ala Gly Gly Ile Arg Pro Gln Phe Gln Phe Gly
            340                 345                 350 cat ccc acg cag cct agg gga ctc acc gtg agg gag ctg gct cgg ctg    1104
His Pro Thr Gln Pro Arg Gly Leu Thr Val Arg Glu Leu Ala Arg Leu
        355                 360                 365 cag agt ttc ccc gat gtg gtg tac ttt cat ggg ggc att gtt caa ggg    1152
Gln Ser Phe Pro Asp Val Val Tyr Phe His Gly Gly Ile Val Gln Gly
    370                 375                 380 cgg gtg cag act ggg aac gcc gtg cct cct ttg atg gca agg gcc ctg    1200
Arg Val Gln Thr Gly Asn Ala Val Pro Pro Leu Met Ala Arg Ala Leu
385                 390                 395                 400 gcg ttg gcg gtg agg gcg gct ctg gag gac ggt ttt gat ccg gag gaa    1248
Ala Leu Ala Val Arg Ala Ala Leu Glu Asp Gly Phe Asp Pro Glu Glu
                405                 410                 415 cac gga gtg ccg ctt cgt agc gca gtt act cgc gtg gca ctc ttc tga    1296
His Gly Val Pro Leu Arg Ser Ala Val Thr Arg Val Ala Leu Phe
```

```
                      420                 425                 430

<210> SEQ ID NO 10
<211> LENGTH: 431
<212> TYPE: PRT
<213> ORGANISM: Thermus sp. R

<400> SEQUENCE: 10

Met Cys Pro Ala Ser Ala Trp Arg Arg Pro Gly Arg Cys Arg Thr
1               5                   10                  15

Trp Trp Asp Lys Val Glu Arg Val Arg Asp Met Ser Cys Val Asn Gln
                20                  25                  30

Leu Asp Pro Trp Asp Pro Lys Arg Leu Pro Glu Glu Ser Pro Tyr Tyr
            35                  40                  45

Trp Lys Gly Ser Pro Gln Val Leu Arg Arg Ser Ser Leu Arg Asp Glu
50                  55                  60

Gly Arg Leu Ile Leu Val Asp Leu Phe Ser Ala Gly Gly Phe Ser
65                  70                  75                  80

Val Gly Phe Glu Gln Ala Gly Phe Val Ser Ala Leu Gly Leu Asp Ile
                85                  90                  95

Tyr Thr Val Ala Ala Lys Thr Phe Met Glu His His Pro Arg Ala Gly
                100                 105                 110

Phe Ile Leu Gly Asp Ala Arg Ala Val Thr Pro Glu Met Leu Leu Glu
            115                 120                 125

Ala Leu Asn Gly Leu Arg Pro His Val Val Thr Gly Gly Val Pro Cys
        130                 135                 140

Gln Arg Phe Ser Leu Thr Asn Arg Lys Arg Asn Asp Glu Asp Pro Arg
145                 150                 155                 160

Asn Tyr Leu Phe Arg Glu Phe Ile Arg Leu Ala Arg Phe Leu Asp Pro
                165                 170                 175

Asp Val Leu Ile Val Glu Asn Val Ser Gly Ile Arg Ser Ala Ala Asn
            180                 185                 190

Gly Lys Phe Val Leu Glu Ile Val Arg Ala Met Glu Glu Ala Gly Tyr
        195                 200                 205

Arg Ala His Val Glu Val Leu Asn Ala Ala Asp Phe Gly Val Pro Gln
210                 215                 220

His Arg Lys Arg Ile Phe Phe Val Gly Val Arg Pro Gly Ile Glu Phe
225                 230                 235                 240

Arg Trp Pro Arg Pro Thr His Gly Pro Leu Gly Glu His Pro Trp Val
                245                 250                 255

Ser Val Trp Glu Ala Ile Gly Asp Leu Pro Pro Leu Gly Pro Gly Glu
            260                 265                 270

Ser Ala His Glu Tyr His Leu Pro Pro Gln Thr Asp Tyr Gln Arg Arg
        275                 280                 285

Met Arg Glu Gly Ala Val Leu Leu Gly Asn His Glu Ser Pro Lys His
    290                 295                 300

Pro Lys Gly Thr Ser Glu Met Ile Ala Asn Thr Pro Gly Glu Pro
305                 310                 315                 320

Met Tyr Glu Lys Phe Arg Gln Arg Ile Arg Leu His Pro Asp Arg Pro
                325                 330                 335

Ser Pro Thr Ile Val Ala Gly Ile Arg Pro Gln Phe Gln Phe Gly
            340                 345                 350

His Pro Thr Gln Pro Arg Gly Leu Thr Val Arg Glu Leu Ala Arg Leu
        355                 360                 365
```

```
Gln Ser Phe Pro Asp Val Val Tyr Phe His Gly Gly Ile Val Gln Gly
    370                 375                 380

Arg Val Gln Thr Gly Asn Ala Val Pro Pro Leu Met Ala Arg Ala Leu
385                 390                 395                 400

Ala Leu Ala Val Arg Ala Ala Leu Glu Asp Gly Phe Asp Pro Glu Glu
                405                 410                 415

His Gly Val Pro Leu Arg Ser Ala Val Thr Arg Val Ala Leu Phe
                420                 425                 430

<210> SEQ ID NO 11
<211> LENGTH: 1566
<212> TYPE: DNA
<213> ORGANISM: Thermus sp. R
<220> FEATURE:
<221> NAME/KEY: CDS
<222> LOCATION: (1)..(1566)
<223> OTHER INFORMATION:

<400> SEQUENCE: 11
```

| | | | | | | | | | | | | | | | | |
|---|---|---|---|---|---|---|---|---|---|---|---|---|---|---|---|---|
| atg | aaa | cgg | agc | gag | atc | gag | gaa | ctt | cta | gaa | atc | ttc | aga | tgc | agt | 48 |
| Met | Lys | Arg | Ser | Glu | Ile | Glu | Glu | Leu | Leu | Glu | Ile | Phe | Arg | Cys | Ser | |
| 1 | | | | 5 | | | | | 10 | | | | | 15 | | |
| ctt | ctc | tcc | atc | cca | tca | ggc | cca | ttc | gcg | agg | cga | gtt | cac | caa | ttc | 96 |
| Leu | Leu | Ser | Ile | Pro | Ser | Gly | Pro | Phe | Ala | Arg | Arg | Val | His | Gln | Phe | |
| | | | 20 | | | | | 25 | | | | | 30 | | | |
| acc | ctc | cac | gga | tac | act | tat | ccc | ttt | gtg | gag | cag | tat | gga | gag | gct | 144 |
| Thr | Leu | His | Gly | Tyr | Thr | Tyr | Pro | Phe | Val | Glu | Gln | Tyr | Gly | Glu | Ala | |
| | | 35 | | | | | 40 | | | | | 45 | | | | |
| gcc | ctg | ccg | gat | cct | cca | ccc | gtg | gag | gta | aca | ggc | cgc | gcc | tcc | cga | 192 |
| Ala | Leu | Pro | Asp | Pro | Pro | Pro | Val | Glu | Val | Thr | Gly | Arg | Ala | Ser | Arg | |
| 50 | | | | | 55 | | | | | 60 | | | | | | |
| cgt | cac | tcc | atg | ctg | gca | gcg | gta | ctt | ttg | gcg | atg | aag | ggt | gac | ttc | 240 |
| Arg | His | Ser | Met | Leu | Ala | Ala | Val | Leu | Leu | Ala | Met | Lys | Gly | Asp | Phe | |
| 65 | | | | 70 | | | | | 75 | | | | | 80 | | |
| ctc | ttt | ttc | ttt | caa | gct | gat | cca | caa | gat | ccc | gag | ttg | ggg | agt | cga | 288 |
| Leu | Phe | Phe | Phe | Gln | Ala | Asp | Pro | Gln | Asp | Pro | Glu | Leu | Gly | Ser | Arg | |
| | | | | 85 | | | | | 90 | | | | | 95 | | |
| aga | ggc | atc | cga | gga | gtc | tat | acc | gtt | aag | ggc | cct | ccc | ggc | cgg | gct | 336 |
| Arg | Gly | Ile | Arg | Gly | Val | Tyr | Thr | Val | Lys | Gly | Pro | Pro | Gly | Arg | Ala | |
| | | | 100 | | | | | 105 | | | | | 110 | | | |
| ggg | cac | acg | aaa | cct | ctg | gaa | cat | ccc | cac | tac | gga | aaa | gac | tac | aaa | 384 |
| Gly | His | Thr | Lys | Pro | Leu | Glu | His | Pro | His | Tyr | Gly | Lys | Asp | Tyr | Lys | |
| | | 115 | | | | | 120 | | | | | 125 | | | | |
| atg | cat | gct | gct | tgc | cct | aaa | tgt | ggg | tcc | cca | ttc | tcc | agc | ctc | tac | 432 |
| Met | His | Ala | Ala | Cys | Pro | Lys | Cys | Gly | Ser | Pro | Phe | Ser | Ser | Leu | Tyr | |
| | 130 | | | | | 135 | | | | | 140 | | | | | |
| ggc | gcg | tgc | cca | gag | tgt | ggg | aat | ccg | ttg | ccg | ttg | cca | cca | aaa | ccc | 480 |
| Gly | Ala | Cys | Pro | Glu | Cys | Gly | Asn | Pro | Leu | Pro | Leu | Pro | Pro | Lys | Pro | |
| 145 | | | | | 150 | | | | | 155 | | | | | 160 | |
| tca | cgc | ttt | ttg | cgc | aaa | ggc | aaa | gaa | cct | ctc | cca | gaa | cac | gtc | ctg | 528 |
| Ser | Arg | Phe | Leu | Arg | Lys | Gly | Lys | Glu | Pro | Leu | Pro | Glu | His | Val | Leu | |
| | | | | 165 | | | | | 170 | | | | | 175 | | |
| agc | gtt | cgc | ctc | ccc | gtc | gaa | ccc | ttc | acc | gtc | ttt | gaa | aga | gag | gtg | 576 |
| Ser | Val | Arg | Leu | Pro | Val | Glu | Pro | Phe | Thr | Val | Phe | Glu | Arg | Glu | Val | |
| | | | 180 | | | | | 185 | | | | | 190 | | | |
| aca | gac | gag | aga | gtc | tat | ggc | gac | atg | agt | tcc | gac | aac | atc | ctg | gat | 624 |
| Thr | Asp | Glu | Arg | Val | Tyr | Gly | Asp | Met | Ser | Ser | Asp | Asn | Ile | Leu | Asp | |
| | | 195 | | | | | 200 | | | | | 205 | | | | |
| cga | gcc | ctc | gtg | tgg | att | ggg | cgc | cac | gac | aac | gca | atg | ggg | gca | ggg | 672 |
| Arg | Ala | Leu | Val | Trp | Ile | Gly | Arg | His | Asp | Asn | Ala | Met | Gly | Ala | Gly | |
| | 210 | | | | | 215 | | | | | 220 | | | | | |

```
aaa ggc agc tcc gtg cgc caa ctc ctg ccg gag gag gcc ctg aga atc     720
Lys Gly Ser Ser Val Arg Gln Leu Leu Pro Glu Glu Ala Leu Arg Ile
225             230                 235                 240 tac aag ctt ctg ctt acg gag tcg gat caa agg ctg aag tcc ctc agc     768
Tyr Lys Leu Leu Leu Thr Glu Ser Asp Gln Arg Leu Lys Ser Leu Ser
                245                 250                 255 tca ccc tca ggg tta cct act ggc cac atc ccc atc cta aat cca gat     816
Ser Pro Ser Gly Leu Pro Thr Gly His Ile Pro Ile Leu Asn Pro Asp
            260                 265                 270 gga acc ccc ctg gag tgc gta ttg aca aca gaa gat tcg tca aag gtt     864
Gly Thr Pro Leu Glu Cys Val Leu Thr Thr Glu Asp Ser Ser Lys Val
        275                 280                 285 aga gaa gaa att tct ata cac acc gcc cta tcc aaa gaa gtg aac aac     912
Arg Glu Glu Ile Ser Ile His Thr Ala Leu Ser Lys Glu Val Asn Asn
    290                 295                 300 cct cat tcg tgc ctt tac aaa agg cta atc ccc aag acc gta cca gga     960
Pro His Ser Cys Leu Tyr Lys Arg Leu Ile Pro Lys Thr Val Pro Gly
305                 310                 315                 320 tta cag aac ctt tgg caa acc cac tac tta gag tac gtc tcc tnt gag    1008
Leu Gln Asn Leu Trp Gln Thr His Tyr Leu Glu Tyr Val Ser Xaa Glu
                325                 330                 335 ttt cct tgg ggt tac acc ggt tcc acc tcc gan tac gtg ctc gtc ttc    1056
Phe Pro Trp Gly Tyr Thr Gly Ser Thr Ser Xaa Tyr Val Leu Val Phe
            340                 345                 350 cgt cct cga gat ggg agc ccg gtt cgg cac gca gtc gtc ata gag ttc    1104
Arg Pro Arg Asp Gly Ser Pro Val Arg His Ala Val Val Ile Glu Phe
        355                 360                 365 aaa agg gac gag gtg ggc att gcg gaa gtg atg cag gct tgg ctt tac    1152
Lys Arg Asp Glu Val Gly Ile Ala Glu Val Met Gln Ala Trp Leu Tyr
    370                 375                 380 atg ccc tgg gtc gcc caa ctt ttg ggc atg cac ttg ggc aac ctc gtc    1200
Met Pro Trp Val Ala Gln Leu Leu Gly Met His Leu Gly Asn Leu Val
385                 390                 395                 400 ggt caa cct ggg cgc ctc gtg gag gtt cac tta aca ccg gtc ctt gtg    1248
Gly Gln Pro Gly Arg Leu Val Glu Val His Leu Thr Pro Val Leu Val
                405                 410                 415 gga gca aga ctg gtg gga aga ggc caa aac cga att cac gtt ttg ccc    1296
Gly Ala Arg Leu Val Gly Arg Gly Gln Asn Arg Ile His Val Leu Pro
            420                 425                 430 agg ggt tat gac cga act gtg acg tac tac aac ggg gct aaa gtc cgc    1344
Arg Gly Tyr Asp Arg Thr Val Thr Tyr Tyr Asn Gly Ala Lys Val Arg
        435                 440                 445 cac gtt gta aat ccc cca gtt ttc tgg gag tac agc ttg aaa ccg tgt    1392
His Val Val Asn Pro Pro Val Phe Trp Glu Tyr Ser Leu Lys Pro Cys
    450                 455                 460 gga tcc agt caa aac aga gca gaa gtt agg ttt tca cca att cat ttg    1440
Gly Ser Ser Gln Asn Arg Ala Glu Val Arg Phe Ser Pro Ile His Leu
465                 470                 475                 480 aac atc aaa acg ata aac tac atc cca cca ata ggc act tcc aca gcc    1488
Asn Ile Lys Thr Ile Asn Tyr Ile Pro Pro Ile Gly Thr Ser Thr Ala
                485                 490                 495 gaa gcc gag cgg aat agg gca ata gaa gag ttc agg agg ctc gcg aaa    1536
Glu Ala Glu Arg Asn Arg Ala Ile Glu Glu Phe Arg Arg Leu Ala Lys
            500                 505                 510 agc ctc tct atg gga atc ccc ctc ctt taa                            1566
Ser Leu Ser Met Gly Ile Pro Leu Leu
        515                 520
```

<210> SEQ ID NO 12

-continued

```
<211> LENGTH: 521
<212> TYPE: PRT
<213> ORGANISM: Thermus sp. R
<220> FEATURE:
<221> NAME/KEY: misc_feature
<222> LOCATION: (335)..(335)
<223> OTHER INFORMATION: Xaa=any amino acid
<220> FEATURE:
<221> NAME/KEY: misc_feature
<222> LOCATION: (347)..(347)
<223> OTHER INFORMATION: Xaa=any amino acid

<400> SEQUENCE: 12

Met Lys Arg Ser Glu Ile Glu Glu Leu Leu Glu Ile Phe Arg Cys Ser
1               5                   10                  15

Leu Leu Ser Ile Pro Ser Gly Pro Phe Ala Arg Arg Val His Gln Phe
            20                  25                  30

Thr Leu His Gly Tyr Thr Tyr Pro Phe Val Glu Gln Tyr Gly Glu Ala
        35                  40                  45

Ala Leu Pro Asp Pro Pro Val Glu Val Thr Gly Arg Ala Ser Arg
    50                  55                  60

Arg His Ser Met Leu Ala Ala Val Leu Leu Ala Met Lys Gly Asp Phe
65                  70                  75                  80

Leu Phe Phe Phe Gln Ala Asp Pro Gln Asp Pro Glu Leu Gly Ser Arg
                85                  90                  95

Arg Gly Ile Arg Gly Val Tyr Thr Val Lys Gly Pro Pro Gly Arg Ala
            100                 105                 110

Gly His Thr Lys Pro Leu Glu His Pro His Tyr Gly Lys Asp Tyr Lys
        115                 120                 125

Met His Ala Ala Cys Pro Lys Cys Gly Ser Pro Phe Ser Ser Leu Tyr
130                 135                 140

Gly Ala Cys Pro Glu Cys Gly Asn Pro Leu Pro Leu Pro Pro Lys Pro
145                 150                 155                 160

Ser Arg Phe Leu Arg Lys Gly Lys Glu Pro Leu Pro Glu His Val Leu
                165                 170                 175

Ser Val Arg Leu Pro Val Glu Pro Phe Thr Val Phe Glu Arg Glu Val
            180                 185                 190

Thr Asp Glu Arg Val Tyr Gly Asp Met Ser Ser Asp Asn Ile Leu Asp
        195                 200                 205

Arg Ala Leu Val Trp Ile Gly Arg His Asp Asn Ala Met Gly Ala Gly
210                 215                 220

Lys Gly Ser Ser Val Arg Gln Leu Leu Pro Glu Glu Ala Leu Arg Ile
225                 230                 235                 240

Tyr Lys Leu Leu Leu Thr Glu Ser Asp Gln Arg Leu Lys Ser Leu Ser
                245                 250                 255

Ser Pro Ser Gly Leu Pro Thr Gly His Ile Pro Ile Leu Asn Pro Asp
            260                 265                 270

Gly Thr Pro Leu Glu Cys Val Leu Thr Thr Glu Asp Ser Ser Lys Val
        275                 280                 285

Arg Glu Glu Ile Ser Ile His Thr Ala Leu Ser Lys Glu Val Asn Asn
    290                 295                 300

Pro His Ser Cys Leu Tyr Lys Arg Leu Ile Pro Lys Thr Val Pro Gly
305                 310                 315                 320

Leu Gln Asn Leu Trp Gln Thr His Tyr Leu Glu Tyr Val Ser Xaa Glu
                325                 330                 335

Phe Pro Trp Gly Tyr Thr Gly Ser Thr Ser Xaa Tyr Val Leu Val Phe
            340                 345                 350
```

-continued

```
Arg Pro Arg Asp Gly Ser Pro Val Arg His Ala Val Ile Glu Phe
        355                 360                 365

Lys Arg Asp Glu Val Gly Ile Ala Glu Val Met Gln Ala Trp Leu Tyr
    370                 375                 380

Met Pro Trp Val Ala Gln Leu Leu Gly Met His Leu Gly Asn Leu Val
385                 390                 395                 400

Gly Gln Pro Gly Arg Leu Val Glu Val His Leu Thr Pro Val Leu Val
                405                 410                 415

Gly Ala Arg Leu Val Gly Arg Gly Gln Asn Arg Ile His Val Leu Pro
            420                 425                 430

Arg Gly Tyr Asp Arg Thr Val Thr Tyr Tyr Asn Gly Ala Lys Val Arg
        435                 440                 445

His Val Val Asn Pro Pro Val Phe Trp Glu Tyr Ser Leu Lys Pro Cys
    450                 455                 460

Gly Ser Ser Gln Asn Arg Ala Glu Val Arg Phe Ser Pro Ile His Leu
465                 470                 475                 480

Asn Ile Lys Thr Ile Asn Tyr Ile Pro Pro Ile Gly Thr Ser Thr Ala
                485                 490                 495

Glu Ala Glu Arg Asn Arg Ala Ile Glu Glu Phe Arg Arg Leu Ala Lys
            500                 505                 510

Ser Leu Ser Met Gly Ile Pro Leu Leu
        515                 520

<210> SEQ ID NO 13
<211> LENGTH: 678
<212> TYPE: DNA
<213> ORGANISM: Thermus sp. R
<220> FEATURE:
<221> NAME/KEY: CDS
<222> LOCATION: (1)..(678)
<223> OTHER INFORMATION:

<400> SEQUENCE: 13 ttg atc cgg agg aac acg gag tgc cgc ttc gta gcg cag tta ctc gcg      48
Leu Ile Arg Arg Asn Thr Glu Cys Arg Phe Val Ala Gln Leu Leu Ala
1               5                   10                  15 tgg cac tct tct gac gcc cat cgt cgt gat gtc ttc tgg tgg agg ggc      96
Trp His Ser Ser Asp Ala His Arg Arg Asp Val Phe Trp Trp Arg Gly
            20                  25                  30 gtt gag gat ccc tat gtt ctt ttc gtt gtt gaa gtg ctc ttg gca cgc     144
Val Glu Asp Pro Tyr Val Leu Phe Val Val Glu Val Leu Leu Ala Arg
        35                  40                  45 act cgc gca gag cgt gtg tcc gaa gtg gcg cgg gaa ctt gtg caa cga     192
Thr Arg Ala Glu Arg Val Ser Glu Val Ala Arg Glu Leu Val Gln Arg
    50                  55                  60 tgg ccc gaa ttc tgc tcg ctt gca aga gct gat gag gct gag ctg gag     240
Trp Pro Glu Phe Cys Ser Leu Ala Arg Ala Asp Glu Ala Glu Leu Glu
65                  70                  75                  80 cag atg ctc cga cct ctg ggt ttc caa agg gtt aga gct tcg gct ctg     288
Gln Met Leu Arg Pro Leu Gly Phe Gln Arg Val Arg Ala Ser Ala Leu
                85                  90                  95 aag aga gcg gca gag gag gtc tgc act cgg tgg ggg ggt aac ctg ccg     336
Lys Arg Ala Ala Glu Glu Val Cys Thr Arg Trp Gly Gly Asn Leu Pro
            100                 105                 110 ctt gaa gag gag aag att gcc tct ctt cca aga tct ggc cgc tat gtg     384
Leu Glu Glu Glu Lys Ile Ala Ser Leu Pro Arg Ser Gly Arg Tyr Val
        115                 120                 125 gca aat gca gtt ttg att tac tcc act tgt gcc agg aag gtg gct gtt     432
```

```
Ala Asn Ala Val Leu Ile Tyr Ser Thr Cys Ala Arg Lys Val Ala Val
        130                 135                 140 gac gtc aat gtg gct cgt gtc gtc tct cgc gtc ttt gga ttt att tta    480
Asp Val Asn Val Ala Arg Val Val Ser Arg Val Phe Gly Phe Ile Leu
145                 150                 155                 160 gtt aat gga aag gac cgg gag gag aac ctt tgg gct ctg gct caa cgt    528
Val Asn Gly Lys Asp Arg Glu Glu Asn Leu Trp Ala Leu Ala Gln Arg
                165                 170                 175 ctt gtt gag tgc aca tct ggt tgc gaa gtg cgc agt tta aat tgg gct    576
Leu Val Glu Cys Thr Ser Gly Cys Glu Val Arg Ser Leu Asn Trp Ala
            180                 185                 190 ctt ttg gac gtt ggg cgc gaa att tgt cac ccg acc aaa cct agg tgt    624
Leu Leu Asp Val Gly Arg Glu Ile Cys His Pro Thr Lys Pro Arg Cys
        195                 200                 205 ccc ctt tgt ccc gtg cgt gag atc tgc cac ttc gcg agg ttc atc cgc    672
Pro Leu Cys Pro Val Arg Glu Ile Cys His Phe Ala Arg Phe Ile Arg
    210                 215                 220 att tag                                                            678
Ile
225

<210> SEQ ID NO 14
<211> LENGTH: 225
<212> TYPE: PRT
<213> ORGANISM: Thermus sp. R

<400> SEQUENCE: 14

Leu Ile Arg Arg Asn Thr Glu Cys Arg Phe Val Ala Gln Leu Leu Ala
1               5                   10                  15

Trp His Ser Ser Asp Ala His Arg Arg Asp Val Phe Trp Trp Arg Gly
                20                  25                  30

Val Glu Asp Pro Tyr Val Leu Phe Val Val Glu Val Leu Leu Ala Arg
            35                  40                  45

Thr Arg Ala Glu Arg Val Ser Glu Val Ala Arg Glu Leu Val Gln Arg
        50                  55                  60

Trp Pro Glu Phe Cys Ser Leu Ala Arg Ala Asp Glu Ala Glu Leu Glu
65                  70                  75                  80

Gln Met Leu Arg Pro Leu Gly Phe Gln Arg Val Arg Ala Ser Ala Leu
                85                  90                  95

Lys Arg Ala Ala Glu Glu Val Cys Thr Arg Trp Gly Gly Asn Leu Pro
            100                 105                 110

Leu Glu Glu Glu Lys Ile Ala Ser Leu Pro Arg Ser Gly Arg Tyr Val
        115                 120                 125

Ala Asn Ala Val Leu Ile Tyr Ser Thr Cys Ala Arg Lys Val Ala Val
        130                 135                 140

Asp Val Asn Val Ala Arg Val Val Ser Arg Val Phe Gly Phe Ile Leu
145                 150                 155                 160

Val Asn Gly Lys Asp Arg Glu Glu Asn Leu Trp Ala Leu Ala Gln Arg
                165                 170                 175

Leu Val Glu Cys Thr Ser Gly Cys Glu Val Arg Ser Leu Asn Trp Ala
            180                 185                 190

Leu Leu Asp Val Gly Arg Glu Ile Cys His Pro Thr Lys Pro Arg Cys
        195                 200                 205

Pro Leu Cys Pro Val Arg Glu Ile Cys His Phe Ala Arg Phe Ile Arg
    210                 215                 220

Ile
225
```

<210> SEQ ID NO 15
<211> LENGTH: 31
<212> TYPE: PRT
<213> ORGANISM: synthetic

<400> SEQUENCE: 15

Lys Gly Asp Phe Leu Phe Phe Phe Gln Ala Asp Pro Gln Asp Pro Glu
1               5                   10                  15

Leu Gly Ser Arg Arg Gly Ile Arg Gly Val Tyr Thr Asx Lys Gly
            20                  25                  30

<210> SEQ ID NO 16
<211> LENGTH: 10
<212> TYPE: PRT
<213> ORGANISM: synthetic

<400> SEQUENCE: 16

Phe Phe Phe Gln Ala Asp Pro Gln Asp Pro
1               5                   10

<210> SEQ ID NO 17
<211> LENGTH: 48
<212> TYPE: DNA
<213> ORGANISM: synthetic

<400> SEQUENCE: 17
tcagcagcat gcggaggttt aaaaatgtgt cccgcaagcg cctggagg            48

<210> SEQ ID NO 18
<211> LENGTH: 36
<212> TYPE: DNA
<213> ORGANISM: synthetic

<400> SEQUENCE: 18
cgacgagtcg actcagaaga gtgccacgcg agtaac                         36

<210> SEQ ID NO 19
<211> LENGTH: 24
<212> TYPE: DNA
<213> ORGANISM: synthetic

<400> SEQUENCE: 19
cggcccagcg ggccctgcac cagt                                      24

<210> SEQ ID NO 20
<211> LENGTH: 24
<212> TYPE: DNA
<213> ORGANISM: synthetic

<400> SEQUENCE: 20
gaggaccacc acccgctcct ttcc                                      24

<210> SEQ ID NO 21
<211> LENGTH: 24
<212> TYPE: DNA
<213> ORGANISM: synthetic

<400> SEQUENCE: 21
cgaatctttt gcgaatgcta tact                                      24

<210> SEQ ID NO 22
<211> LENGTH: 24

```
<210> SEQ ID NO 22
<211> LENGTH: 24
<212> TYPE: DNA
<213> ORGANISM: synthetic

<400> SEQUENCE: 22
gagggaagcc cagaccgagg aaga                                              24

<210> SEQ ID NO 23
<211> LENGTH: 39
<212> TYPE: DNA
<213> ORGANISM: synthetic

<400> SEQUENCE: 23
ctcatcattc atatgtctgg tggtcaagga aaagccgtg                              39

<210> SEQ ID NO 24
<211> LENGTH: 39
<212> TYPE: DNA
<213> ORGANISM: synthetic

<400> SEQUENCE: 24
gcttgggcca agcttttgat ggtcagcagg agcttgcct                              39

<210> SEQ ID NO 25
<211> LENGTH: 23
<212> TYPE: DNA
<213> ORGANISM: synthetic

<400> SEQUENCE: 25 gtgtccccttt tgtcccgtgc gtg                                              23

<210> SEQ ID NO 26
<211> LENGTH: 24
<212> TYPE: DNA
<213> ORGANISM: Escherichia coli

<400> SEQUENCE: 26
ctaggtttgg tcgggtgaca aatt                                              24

<210> SEQ ID NO 27
<211> LENGTH: 33
<212> TYPE: PRT
<213> ORGANISM: Escherichia coli
<220> FEATURE:
<221> NAME/KEY: MISC_FEATURE
<222> LOCATION: (15)..(15)
<223> OTHER INFORMATION: Xaa=unknown amino acid
<220> FEATURE:
<221> NAME/KEY: MISC_FEATURE
<222> LOCATION: (24)..(24)
<223> OTHER INFORMATION: Asp = erroneous calling
<220> FEATURE:
<221> NAME/KEY: MISC_FEATURE
<222> LOCATION: (26)..(26)
<223> OTHER INFORMATION: Xaa = omitted amino acid calling

<400> SEQUENCE: 27

Met Lys Arg Ser Glu Ile Glu Glu Leu Leu Glu Ile Phe Arg Xaa Ser
1               5                   10                  15

Leu Leu Ser Ile Pro Ser Gly Asp Phe Xaa Arg Arg Val His Gln Phe
            20                  25                  30

Thr

<210> SEQ ID NO 28
<211> LENGTH: 8
<212> TYPE: PRT
```

<213> ORGANISM: Escherichia coli

<400> SEQUENCE: 28

Met Lys Arg Ser Glu Ile Glu Glu
1               5

<210> SEQ ID NO 29
<211> LENGTH: 32
<212> TYPE: DNA
<213> ORGANISM: Escherichia coli
<220> FEATURE:
<221> NAME/KEY: misc_feature
<222> LOCATION: (15)..(15)
<223> OTHER INFORMATION: R=A or G
<220> FEATURE:
<221> NAME/KEY: misc_feature
<222> LOCATION: (18)..(18)
<223> OTHER INFORMATION: R=A or G
<220> FEATURE:
<221> NAME/KEY: misc_feature
<222> LOCATION: (24)..(24)
<223> OTHER INFORMATION: R=A or G
<220> FEATURE:
<221> NAME/KEY: misc_feature
<222> LOCATION: (30)..(30)
<223> OTHER INFORMATION: R=A or G
<220> FEATURE:
<221> NAME/KEY: misc_feature
<222> LOCATION: (21)..(21)
<223> OTHER INFORMATION: N=G, A, C or T

<400> SEQUENCE: 29
cgcggatcca tgaaragrtc ngaratcgar ga                                    32

<210> SEQ ID NO 30
<211> LENGTH: 33
<212> TYPE: DNA
<213> ORGANISM: Escherichia coli
<220> FEATURE:
<221> NAME/KEY: misc_feature
<222> LOCATION: (15)..(15)
<223> OTHER INFORMATION: R=A or G
<220> FEATURE:
<221> NAME/KEY: misc_feature
<222> LOCATION: (25)..(25)
<223> OTHER INFORMATION: R=A or G
<220> FEATURE:
<221> NAME/KEY: misc_feature
<222> LOCATION: (31)..(31)
<223> OTHER INFORMATION: R=A or G
<220> FEATURE:
<221> NAME/KEY: misc_feature
<222> LOCATION: (22)..(22)
<223> OTHER INFORMATION: N=G, A, C or T

<400> SEQUENCE: 30
cgcggatcca tgaarcggct cngaratcga rga                                   33

<210> SEQ ID NO 31
<211> LENGTH: 32
<212> TYPE: DNA
<213> ORGANISM: Escherichia coli
<220> FEATURE:
<221> NAME/KEY: misc_feature
<222> LOCATION: (15)..(15)
<223> OTHER INFORMATION: R=A or G
<220> FEATURE:
<221> NAME/KEY: misc_feature
<222> LOCATION: (24)..(24)
<223> OTHER INFORMATION: R=A or G
<220> FEATURE:
<221> NAME/KEY: misc_feature
<222> LOCATION: (30)..(30)

```
<223> OTHER INFORMATION: R=A or G
<220> FEATURE:
<221> NAME/KEY: misc_feature
<222> LOCATION: (18)..(18)
<223> OTHER INFORMATION: R=A or G
<220> FEATURE:
<221> NAME/KEY: misc_feature
<222> LOCATION: (21)..(21)
<223> OTHER INFORMATION: Y=C or T

<400> SEQUENCE: 31
cgcggatcca tgaaragrag ygaratcgar ga                                    32

<210> SEQ ID NO 32
<211> LENGTH: 33
<212> TYPE: DNA
<213> ORGANISM: Escherichia coli
<220> FEATURE:
<221> NAME/KEY: misc_feature
<222> LOCATION: (15)..(15)
<223> OTHER INFORMATION: R=A or G
<220> FEATURE:
<221> NAME/KEY: misc_feature
<222> LOCATION: (25)..(25)
<223> OTHER INFORMATION: R=A or G
<220> FEATURE:
<221> NAME/KEY: misc_feature
<222> LOCATION: (31)..(31)
<223> OTHER INFORMATION: R=A or G
<220> FEATURE:
<221> NAME/KEY: misc_feature
<222> LOCATION: (22)..(22)
<223> OTHER INFORMATION: Y=C or T

<400> SEQUENCE: 32
cgcggatcca tgaarcggca gygaratcga rga                                   33

<210> SEQ ID NO 33
<211> LENGTH: 7
<212> TYPE: PRT
<213> ORGANISM: Escherichia coli
<220> FEATURE:
<221> NAME/KEY: misc_feature
<222> LOCATION: (4)..(4)
<223> OTHER INFORMATION: Asp=erroneous calling

<400> SEQUENCE: 33

Pro Ser Gly Asp Phe Arg Arg
1               5

<210> SEQ ID NO 34
<211> LENGTH: 20
<212> TYPE: DNA
<213> ORGANISM: Escherichia coli
<220> FEATURE:
<221> NAME/KEY: misc_feature
<222> LOCATION: (3)..(3)
<223> OTHER INFORMATION: N=G, A, C or T
<220> FEATURE:
<221> NAME/KEY: misc_feature
<222> LOCATION: (12)..(12)
<223> OTHER INFORMATION: N=G, A, C or T
<220> FEATURE:
<221> NAME/KEY: misc_feature
<222> LOCATION: (18)..(18)
<223> OTHER INFORMATION: N=G, A, C or T
<220> FEATURE:
<221> NAME/KEY: misc_feature
<222> LOCATION: (6)..(6)
<223> OTHER INFORMATION: R=A or G
<220> FEATURE:
<221> NAME/KEY: misc_feature
<222> LOCATION: (9)..(9)
```

```
<223> OTHER INFORMATION: R=A or G
<220> FEATURE:
<221> NAME/KEY: misc_feature
<222> LOCATION: (15)..(15)
<223> OTHER INFORMATION: R=A or G

<400> SEQUENCE: 34
cgncgraart cnccrctngg                                          20

<210> SEQ ID NO 35
<211> LENGTH: 20
<212> TYPE: DNA
<213> ORGANISM: Escherichia coli
<220> FEATURE:
<221> NAME/KEY: misc_feature
<222> LOCATION: (3)..(3)
<223> OTHER INFORMATION: N=G, A, C or T
<220> FEATURE:
<221> NAME/KEY: misc_feature
<222> LOCATION: (6)..(6)
<223> OTHER INFORMATION: N=G, A, C or T
<220> FEATURE:
<221> NAME/KEY: misc_feature
<222> LOCATION: (9)..(9)
<223> OTHER INFORMATION: N=G, A, C or T
<220> FEATURE:
<221> NAME/KEY: misc_feature
<222> LOCATION: (12)..(12)
<223> OTHER INFORMATION: Y=C or T
<220> FEATURE:
<221> NAME/KEY: misc_feature
<222> LOCATION: (15)..(15)
<223> OTHER INFORMATION: Y=C or T
<220> FEATURE:
<221> NAME/KEY: misc_feature
<222> LOCATION: (18)..(18)
<223> OTHER INFORMATION: N=G, A, C or T

<400> SEQUENCE: 35
ccntcnggng ayttycgncg                                          20

<210> SEQ ID NO 36
<211> LENGTH: 7
<212> TYPE: PRT
<213> ORGANISM: Escherichia coli
<220> FEATURE:
<221> NAME/KEY: MISC_FEATURE
<222> LOCATION: (4)..(4)
<223> OTHER INFORMATION: Asp=erroneous calling

<400> SEQUENCE: 36

Pro Ser Gly Asp Phe Arg Arg
1               5

<210> SEQ ID NO 37
<211> LENGTH: 8
<212> TYPE: PRT
<213> ORGANISM: Escherichia coli

<400> SEQUENCE: 37

Pro Ser Gly Pro Phe Ala Arg Arg
1               5

<210> SEQ ID NO 38
<211> LENGTH: 31
<212> TYPE: PRT
<213> ORGANISM: Escherichia coli

<400> SEQUENCE: 38

Lys Gly Asp Phe Leu Phe Phe Phe Gln Ala Asp Pro Gln Asp Pro Glu
```

```
1               5               10              15
Leu Gly Ser Arg Arg Gly Ile Arg Gly Val Tyr Thr Val Lys Gly
            20              25              30

<210> SEQ ID NO 39
<211> LENGTH: 10
<212> TYPE: PRT
<213> ORGANISM: Escherichia coli

<400> SEQUENCE: 39

Phe Phe Phe Gln Ala Asp Pro Gln Asp Pro
1               5                   10

<210> SEQ ID NO 40
<211> LENGTH: 49
<212> TYPE: PRT
<213> ORGANISM: Escherichia coli
<220> FEATURE:
<221> NAME/KEY: MISC_FEATURE
<222> LOCATION: (46)..(46)
<223> OTHER INFORMATION: Xaa=unknown amino acid

<400> SEQUENCE: 40

His Leu Gly Asn Leu Val Gly Gln Pro Gly Arg Leu Val Glu Val His
1               5                   10                  15

Leu Thr Pro Val Leu Val Gly Ala Arg Leu Val Gly Arg Gly Gln Asn
            20              25              30

Arg Ile His Val Leu Pro Arg Gly Tyr Asp Arg Thr Val Xaa Tyr Tyr
        35              40              45

Asn

<210> SEQ ID NO 41
<211> LENGTH: 22
<212> TYPE: PRT
<213> ORGANISM: Escherichia coli

<400> SEQUENCE: 41

Met Gly Ala Gly Lys Gly Ser Ser Val Arg Gln Leu Leu Pro Glu Glu
1               5                   10                  15

Ala Leu Gly Ile Tyr Lys
            20

<210> SEQ ID NO 42
<211> LENGTH: 20
<212> TYPE: DNA
<213> ORGANISM: Escherichia coli
<220> FEATURE:
<221> NAME/KEY: misc_feature
<222> LOCATION: (3)..(3)
<223> OTHER INFORMATION: R=A or G
<220> FEATURE:
<221> NAME/KEY: misc_feature
<222> LOCATION: (12)..(12)
<223> OTHER INFORMATION: R=A or G
<220> FEATURE:
<221> NAME/KEY: misc_feature
<222> LOCATION: (6)..(6)
<223> OTHER INFORMATION: Y=C or T
<220> FEATURE:
<221> NAME/KEY: misc_feature
<222> LOCATION: (18)..(18)
<223> OTHER INFORMATION: Y=C or T
<220> FEATURE:
<221> NAME/KEY: misc_feature
<222> LOCATION: (9)..(9)
<223> OTHER INFORMATION: N=G, A, C or T
<220> FEATURE:
```

```
<221> NAME/KEY: misc_feature
<222> LOCATION: (15)..(15)
<223> OTHER INFORMATION: N=G, A, C or T

<400> SEQUENCE: 42
ggrtcytgng grtcngcytg                                               20

<210> SEQ ID NO 43
<211> LENGTH: 20
<212> TYPE: DNA
<213> ORGANISM: Escherichia coli
<220> FEATURE:
<221> NAME/KEY: misc_feature
<222> LOCATION: (3)..(3)
<223> OTHER INFORMATION: R=A or G
<220> FEATURE:
<221> NAME/KEY: misc_feature
<222> LOCATION: (12)..(12)
<223> OTHER INFORMATION: R=A or G
<220> FEATURE:
<221> NAME/KEY: misc_feature
<222> LOCATION: (15)..(15)
<223> OTHER INFORMATION: R=A or G
<220> FEATURE:
<221> NAME/KEY: misc_feature
<222> LOCATION: (18)..(18)
<223> OTHER INFORMATION: R=A or G
<220> FEATURE:
<221> NAME/KEY: misc_feature
<222> LOCATION: (6)..(6)
<223> OTHER INFORMATION: N=C, A, G, or T
<220> FEATURE:
<221> NAME/KEY: misc_feature
<222> LOCATION: (9)..(9)
<223> OTHER INFORMATION: Y=C or T

<400> SEQUENCE: 43
ggrtcngcyt graaraaraa                                               20

<210> SEQ ID NO 44
<211> LENGTH: 33
<212> TYPE: PRT
<213> ORGANISM: Escherichia coli

<400> SEQUENCE: 44

Met Lys Arg Ser Glu Ile Glu Glu Leu Leu Glu Ile Phe Arg Cys Ser
1               5                   10                  15

Leu Leu Ser Ile Pro Ser Gly Pro Phe Ala Arg Arg Val His Gln Phe
            20                  25                  30

Thr

<210> SEQ ID NO 45
<211> LENGTH: 45
<212> TYPE: DNA
<213> ORGANISM: Escherichia coli

<400> SEQUENCE: 45
cgcggatccc atatgaaacg gagcgagatc gaggaacttc tagaa                   45

<210> SEQ ID NO 46
<211> LENGTH: 42
<212> TYPE: DNA
<213> ORGANISM: Escherichia coli

<400> SEQUENCE: 46
tgggtcgacg agctcttaaa ggagggggat tcccatagag ag                      42
```

```
<210> SEQ ID NO 47
<211> LENGTH: 42
<212> TYPE: DNA
<213> ORGANISM: Escherichia coli

<400> SEQUENCE: 47
tggccccacc atatgttaaa ggagggggat tcccatagag ag                        42

<210> SEQ ID NO 48
<211> LENGTH: 42
<212> TYPE: DNA
<213> ORGANISM: Escherichia coli

<400> SEQUENCE: 48
cgcgtaggcc atatgaaacg gagcgagatc gaggaacttc ta                        42
```